United States Patent
Takaai et al.

(10) Patent No.: US 9,321,855 B2
(45) Date of Patent: Apr. 26, 2016

(54) METHOD FOR PRODUCING WATER ABSORBENT RESIN

(75) Inventors: Toshihiro Takaai, Himeji (JP); Shinichi Fujino, Himeji (JP); Hidenori Wada, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 790 days.

(21) Appl. No.: 13/574,281

(22) PCT Filed: Jan. 20, 2011

(86) PCT No.: PCT/JP2011/051004
§ 371 (c)(1),
(2), (4) Date: Jul. 20, 2012

(87) PCT Pub. No.: WO2011/090130
PCT Pub. Date: Jul. 28, 2011

(65) Prior Publication Data
US 2012/0296057 A1    Nov. 22, 2012

(30) Foreign Application Priority Data
Mar. 31, 2010    (JP) ................. 2010-084024

(51) Int. Cl.
*C08J 9/28*    (2006.01)
*C08F 6/00*    (2006.01)
(Continued)

(52) U.S. Cl.
CPC ............... *C08F 6/008* (2013.01); *A61L 15/60* (2013.01); *B01J 20/267* (2013.01);
(Continued)

(58) Field of Classification Search
CPC .......... C08F 6/006; C08F 6/008; C08F 20/04; C08F 20/06; C08J 3/12; C08J 9/28; C08J 2300/14; C08J 2333/02
See application file for complete search history.

(56) References Cited

U.S. PATENT DOCUMENTS 4,920,202 A    4/1990    Irie et al.
5,005,771 A    4/1991    Pieh et al.
(Continued)

FOREIGN PATENT DOCUMENTS

JP    54-053165    4/1979
JP    57-198714    12/1982
(Continued)

OTHER PUBLICATIONS

Fredric L. Buchholz and Andrew T. Graham, The Modern Superabsorbent Polymer Technology (1998), pp. 87-93.

*Primary Examiner* — Richard A Huhn
(74) *Attorney, Agent, or Firm* — Cesari and McKenna LLP

(57) ABSTRACT

In a method for producing a water absorbent resin by drying a particulate hydrogel having a high solid content concentration (of 45% by weight or more, preferably 50% by weight or more, and more preferably 55% by weight or more), a method for efficient drying water absorbent resin having maintained/improved physical properties is provided. Disclosed is a method for producing a water absorbent resin, comprising: a polymerization step to polymerize an unsaturated monomer, and; a drying step to dry a particulate hydrogel crosslinked polymer, which is obtained by micronization of a hydrogel polymer during or after the polymerization and which has a solid content concentration of 45% by weight or more, wherein, an amount of a peroxide in the particulate hydrogel crosslinked polymer to be dried in the drying step is 1 to 100 ppm relative to the weight of the solid content of the particulate hydrogel crosslinked polymer, and a drying temperature of the particulate hydrogel crosslinked polymer in the drying step is 160° C. or more.

16 Claims, 1 Drawing Sheet

(51) Int. Cl.
*A61L 15/60* (2006.01)
*B01J 20/26* (2006.01)
*B01J 20/28* (2006.01)
*C08J 3/24* (2006.01)
*C08F 20/06* (2006.01)
*C08F 20/04* (2006.01)
*C08J 3/12* (2006.01)

(52) U.S. Cl.
CPC ..... *B01J 20/28004* (2013.01); *B01J 20/28047* (2013.01); *C08J 3/245* (2013.01); *B01J 2220/68* (2013.01); *C08F 6/006* (2013.01); *C08F 20/04* (2013.01); *C08F 20/06* (2013.01); *C08J 3/12* (2013.01); *C08J 9/28* (2013.01); *C08J 2300/14* (2013.01); *C08J 2333/02* (2013.01)

(56) References Cited

U.S. PATENT DOCUMENTS

| | | | |
|---|---|---|---|
| 5,075,344 A * | 12/1991 | Johnson | 521/140 |
| 5,229,487 A | 7/1993 | Tsubakimoto et al. | |
| 5,945,495 A | 8/1999 | Daniel et al. | |
| 6,187,902 B1 | 2/2001 | Yanase et al. | |
| 6,207,796 B1 | 3/2001 | Dairoku et al. | |
| 6,291,636 B1 | 9/2001 | Miyake et al. | |
| 6,297,335 B1 * | 10/2001 | Funk et al. | 526/317.1 |
| 6,641,064 B1 | 11/2003 | Dentler et al. | |
| 6,906,159 B2 | 6/2005 | Dairoku et al. | |
| 7,682,702 B2 | 3/2010 | Nitschke | |
| 7,960,490 B2 | 6/2011 | Funk et al. | |
| 2004/0110006 A1 | 6/2004 | Ishizaki et al. | |
| 2005/0051925 A1 * | 3/2005 | Gartner | B01J 3/006 264/211.24 |
| 2007/0123624 A1 | 5/2007 | Otten et al. | |
| 2008/0021150 A1 | 1/2008 | Becker et al. | |
| 2008/0188586 A1 * | 8/2008 | Bruhns et al. | 522/153 |
| 2008/0214749 A1 | 9/2008 | Weismantel et al. | |
| 2008/0287631 A1 | 11/2008 | Nitschke | |
| 2009/0208748 A1 | 8/2009 | Torii et al. | |
| 2009/0298685 A1 | 12/2009 | Torii et al. | |
| 2010/0001233 A1 | 1/2010 | Funk et al. | |
| 2010/0016522 A1 | 1/2010 | Stueven et al. | |
| 2010/0041549 A1 | 2/2010 | Weismantel et al. | |
| 2010/0249320 A1 | 9/2010 | Matsumoto et al. | |

FOREIGN PATENT DOCUMENTS

| | | |
|---|---|---|
| JP | 7-270070 | 10/1995 |
| JP | 8-073518 | 3/1996 |
| JP | 10-059534 | 3/1998 |
| JP | 2000-143720 | 5/2000 |
| JP | 2001-018222 | 1/2001 |
| JP | 2002-226599 | 8/2002 |
| JP | 2003-012812 | 1/2003 |
| JP | 2006-160774 | 6/2006 |
| JP | 2007-224224 | 9/2007 |
| JP | 2009-531467 | 9/2009 |
| WO | 2007/057350 | 5/2007 |
| WO | 2007/116778 | 10/2007 |
| WO | 2008/034786 | 3/2008 |
| WO | 2008/037676 | 4/2008 |
| WO | 2008/087114 | 7/2008 |
| WO | 2009/028568 | 3/2009 |

* cited by examiner

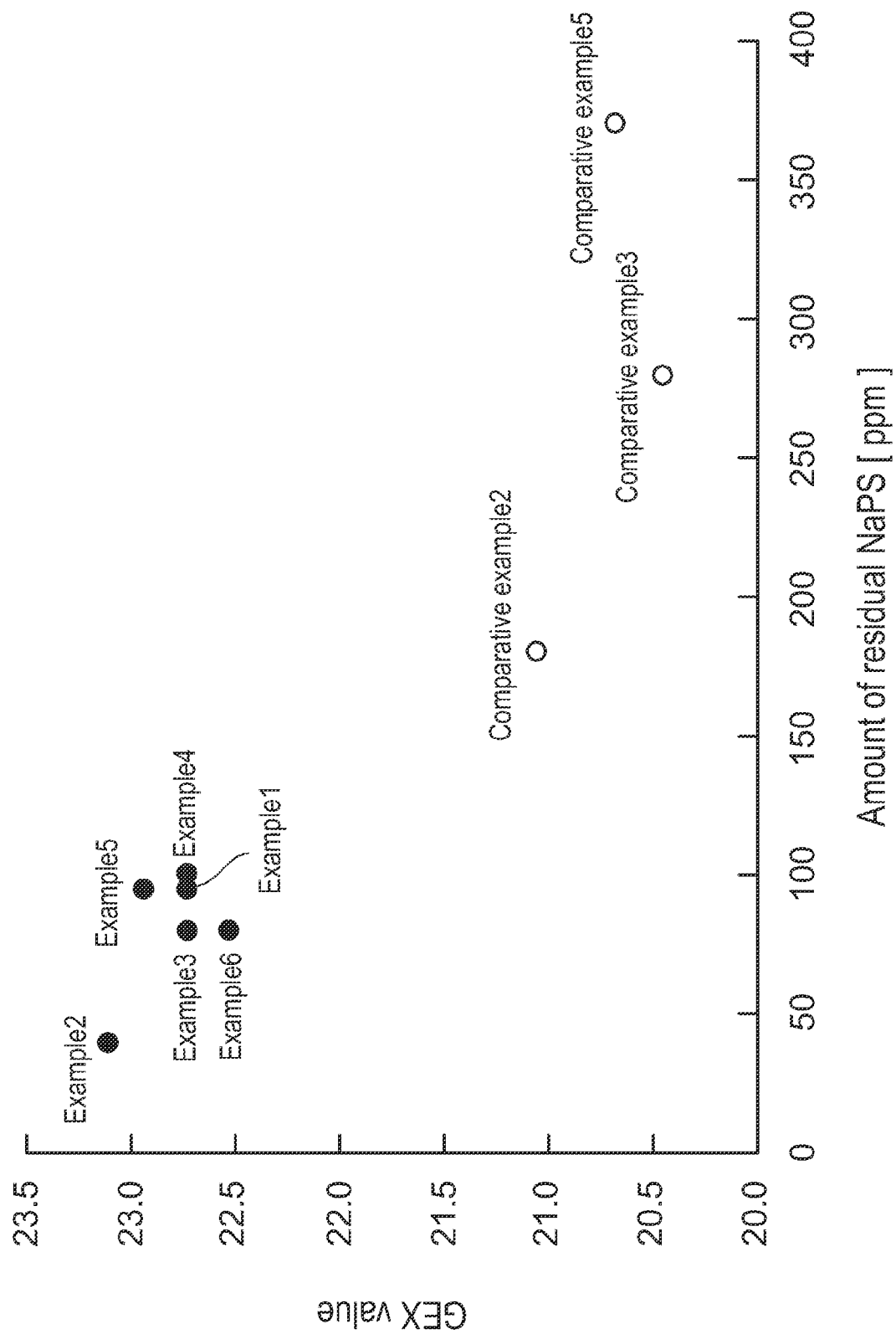

METHOD FOR PRODUCING WATER ABSORBENT RESIN

CROSS REFERENCE TO RELATED APPLICATIONS

This application is a National Stage of International Application No. PCT/JP2011/051004, filed on Jan. 20, 2011, which claims priority to Japanese Application No. 2010-009812 filed Jan. 20, 2010, and Japanese Application No. 2010-084024 filed Mar. 31, 2010. The content of the prior applications are incorporated herein by reference in their entirety.

TECHNICAL FIELD

The present invention relates to a method for producing a water absorbent resin. More specifically, it relates to improvement of a drying method for efficiently providing a water absorbent resin with physical property maintained and improved in high concentration polymerization (a polymerization method with a solid content concentration preferably of 45% or more by weight, more preferably of 50% or more by weight, and still more preferably of 55% or more by weight).

BACKGROUND ART

A water absorbent resin (SAP/Super Absorbent Polymer) is a water swellable and water insoluble polymeric gellant, which is widely and mainly used in disposable articles including an absorbing article such as a disposable diaper, a sanitary napkin, an agricultural and horticultural water retaining agent, and an industrial water stopping agent. As a material for the water absorbent resin, varieties of monomers and hydrophilic polymers have been proposed. Among them, a polyacrylic acid (salt)-type water absorbent resin, which is formed by using acrylic acid and/or a salt thereof as a monomer, is widely used in industrial purposes due to its high water absorption performance. For polymerization of acrylic acid, a radical polymerization initiator such as persulfate salt, hydrogen peroxide, organic peroxide, water extractable azo initiator, and UV polymerization initiator is generally used. Among them, the radical polymerization using sodium persulfate or the like is disclosed in the following Patent Literature or the examples included therein.

The water absorbent resin can be obtained by micronizing a hydrogel crosslinked polymer, which is obtained by polymerizing an aqueous monomer solution, either during or after polymerization, then, drying the particulate hydrogel crosslinked polymer obtained (Non-Patent Literature 1).

As for the method of drying water absorbent resin, a method of using a belt type dryer (Patent Literatures 1 to 5), a method of thin film drying by using a drum dryer or the like (Patent Literature 6), a method for azeotropic dehydration in an organic solvent (Patent Literature 7), a method for drying in fluidized bed (Patent Literature 8), a method for drying in a bed fluid ized by vibrating (Patent Literature 9), and a method for drying under stirring by using a rotor (Patent Literature 10), or the like are known.

As a condition for drying water absorbent resin, a method of controlling dew point or temperature (Patent Literatures 11 and 12) and a method of crushing during drying to dry under stirring (Patent Literature 13), or the like have been suggested for improving physical properties (for example, reducing residual monomers, increasing water absorption capacity, and reducing water extractable components).

Further, since non-dried products may occur during drying of a water absorbent resin to cause excessive load on crushing, a method for removing non-dried products is also known (Patent Literatures 14 to 16). To prevent occurrence of non-dried products, a method of regulating fluidity of a polymer gel (Patent Literature 17), a method of using a gel floating device in a dryer (Patent Literatures 18 and 19), a method of drying by using a specific apparatus for supplying constant quantity of a gel to a dryer (Patent Literature 20), a method of using infrared or the like in combination with hot air (Patent Literature 21) are known. Further, for improvement of drying efficiency, a method of adding a surfactant or an inorganic fine particle to hydrogel (Patent Literatures 22 to 26) is also known. A drying method for hydrogel with low neutralization rate is also known (Patent Literature 27). Still further, a method of drying at 100 to 250° C. with the index of thermally decomposable radical polymerization initiator content at 40 to 100 in a hydrogel before drying is known (Patent Literature 28).

CITATION LIST

Patent Literature

Patent Literature 1: US Patent Application Publication No. 2008/214,749
Patent Literature 2: WO 2008/087114
Patent Literature 3: WO 2008/037676
Patent Literature 4: Japanese Patent Application Laid-Open (JP-A) No. 8-073518
Patent Literature 5: JP-A No. 7-270070
Patent Literature 6: JP-A No. 54-053165
Patent Literature 7: JP-A No. 57-198714
Patent Literature 8: U.S. Pat. No. 6,906,159
Patent Literature 9: JP-A No. 2001-018222
Patent Literature 10: U.S. Pat. No. 5,005,771
Patent Literature 11: U.S. Pat. No. 4,920,202
Patent Literature 12: U.S. Pat. No. 6,207,796
Patent Literature 13: U.S. Pat. No. 6,187,902
Patent Literature 14: U.S. Pat. No. 6,291,636
Patent Literature 15: U.S. Pat. No. 6,641,064
Patent Literature 16: WO 2007/057350
Patent Literature 17: US Patent Application Publication No. 2008/0,021,150
Patent Literature 18: JP-A No. 10-059534
Patent Literature 19: U.S. Pat. No. 5,229,487
Patent Literature 20: JP-A No. 2003-012812
Patent Literature 21: JP-A No. 2007-224224
Patent Literature 22: JP-A No. 2000-143720
Patent Literature 23: JP-A No. 2002-226599
Patent Literature 24: US Patent Application Publication No. 2007/123,624
Patent Literature 25: JP-A No. 2006-160774
Patent Literature 26: U.S. Pat. No. 5,945,495
Patent Literature 27: WO 2008/034786
Patent Literature 28: WO 2007/116778

Non Patent Literature

Non Patent Literature 1: The Modern Superabsorbent Polymer Technology (1998), p. 87 to 93 and others.

SUMMARY OF INVENTION

Technical Problem

In recent years, production scale of a water absorbent resin gradually increases due to increasing demand for a disposable diaper or the like. There is also a tendency that scaling up per line or increasing the polymerization concentration (using an aqueous monomer solution of higher concentration or the like) is desired.

Accompanied by an increase in production scale, however, deterioration of physical properties or a trouble associated with scaling up also occurs frequently. For example, according to the drying step represented by Patent Literatures 1 to 13 described above, generation of non-dried products caused by scaling up or deterioration of physical properties due to excessive drying was observed. Removal of non-dried product (non-dried gel) disclosed in Patent Literatures 14 to 16 and others requires an additional step, thus it is accompanied with cost increase or complex plant operation. Use of other additives disclosed in Patent Literatures 22 to 26 and others may be also has a problem like deterioration of physical properties of a water absorbent resin caused by other additives (for example, lowered surface tension, lowered absorbency under pressure, coloration, or the like) as well as cost increase. The method disclosed in Patent Literatures 17 to 21 also requires an additional expensive device or an additional step for a dryer and the drying method of Patent Literature 27 is limited to a lowly neutralized water absorbent resin having neutralization rate of 55% by mole or less, and it may not be applied to a common water absorbent resin (for example, a resin with neutralization rate of 60 to 80% by mole). The drying method of Patent Literature 28 may also have a problem of coloration due to use of an increased amount of persulfate salt. In accordance with production amount increase of a water absorbent resin, shortening of the polymerization time or drying time has been tried under the purpose of improving productivity. However, such productivity improvement is generally associated with deterioration of physical properties of a water absorbent resin.

The above problem is particularly significant when a hydrogel having higher solid content concentration is dried (hydrogel crosslinked polymer after polymerization). In other words, although it is well known according to conventional production of a water absorbent resin that monomer concentration is increased to 20% by weight, 30% by weight, 40% by weight, or 50% by weight during polymerization for productivity improvement, cost reduction, and energy reduction during production step ($CO_2$ emission amount reduction) and others. However, there is a problem that physical properties of the water absorbent resin to be obtained are greatly deteriorated in general when higher monomer concentration is used (lowered absorbency and increased water extractable content), or the like. Thus, it is clear that concentration increase during polymerization yields sacrifice of physical properties.

Accordingly, provided by the invention is a method for efficient drying of a water absorbent resin with the same or improved physical properties, which is used in a method for producing a water absorbent resin by drying particulate hydrogel having a high solid content concentration (45% by weight or more, preferably 50% by weight or more, and more preferably 55% by weight or more).

Solution to Problem

Inventors of the invention studied to solve the problems described above, and as a result found that, physical properties of a hydrogel after polymerization are not much lowered even when polymerization is carried out at high monomer concentration, but a huge decrease in physical properties is resulted when such hydrogel with a high concentration is dried. Specifically, the problem of deterioration of physical properties of a water absorbent resin depending on increased monomer concentration during polymerization is mostly caused by deterioration of physical properties during drying with high concentration (deteriorated physical properties of a hydrogel after polymerization, in particular, water absorption capacity and water extractables of a dried product, and below-described GEX value representing correlation between them) rather than deterioration of physical properties during high concentration polymerization (deteriorated physical properties of a hydrogel after polymerization, in particular water absorption capacity and water extractables content of gel).

To solve the problems described above, the inventors earnestly studied. It was consequently found that, in the case that water soluble peroxides are used as a radical polymerization initiator for a polymerization step, the problems can be solved by reducing the water soluble peroxides remaining in hydrogel to a predetermined amount or less relative to the solid content in the hydrogel when the obtained hydrogel is dried with hot air at high temperature.

To be specific, conventionally, although use of persulfate salts such as sodium persulfate as a polymerization initiator for polymerization of polyacrylic acid (salt)-type water absorbent resin has been already disclosed in the above Patent Literatures or the examples included therein, it is found that most of the persulfate salt (for example, sodium persulfate/half life at 90° C. of 1.24 hours) remains in a hydrogel crosslinked polymer after the polymerization. It is also found that, for a conventional case of using persulfate salt for polymerization, the hydrogel crosslinked polymer containing persulfate salt in an amount of several hundred ppm to several thousand ppm is supplied to a drying step and deterioration of physical properties during drying is caused by drying of hydrogel crosslinked polymer containing a large amount of persulfate salt. It was particularly found that, when the hydrogel crosslinked polymer having solid content concentration of 45% by weight or more is dried at a temperature of 160° C. or higher, the physical properties are significantly deteriorated. Then, by controlling the persulfate salt content in a hydrogel crosslinked polymer which has solid content concentration of 45% by weight or more before drying, the invention is completed accordingly.

That is, a method for producing a water absorbent resin, comprising: a polymerization step to polymerize an unsaturated monomer, and; a drying step to dry a particulate hydrogel crosslinked polymer, which is obtained by micronization of a hydrogel crosslinked polymer during or after the polymerization and which has a solid content concentration of 45% by weight or more, wherein, an amount of a peroxide in the particulate hydrogel crosslinked polymer to be dried in the drying step is not more than 100 ppm relative to the weight of the solid content of the particulate hydrogel crosslinked polymer, and, a drying temperature of the particulate hydrogel crosslinked polymer in the drying step is 160° C. or more.

The present invention also provides a polyacrylic acid-type water absorbent resin wherein a water absorption capacity (CRC) is 5 [g/g] or more, a residual monomer is 200 ppm or less, a saline flow conductivity (SFC) is 100 [$\times 10^{-7} \cdot cm \cdot s \cdot g^{-1}$] or more, and an amount of peroxide is 1 ppm or less.

Advantageous Effects of Invention

By a simple method of controlling the amount of water soluble peroxides, which are remained in the hydrogel before drying, without requiring modification of reacting materials or investment of expensive facilities, deterioration of physical properties of a water absorbent resin obtained from a hydrogel with high solid content concentration can be suppressed.

BRIEF DESCRIPTION OF DRAWINGS

FIG. 1 is a graph illustrating the relation between GEX value and the amount of water soluble peroxides that are remained in the particulate hydrogel crosslinked polymer before drying.

BEST MODE FOR CARRYING OUT THE INVENTION

Herein below, the method for producing a water absorbent resin of the invention is described in greater detail, but the scope of the invention is not limited to this, and the invention may be altered in many variations as long as the range of the entity of the invention is not impaired. Specifically, the invention is not limited to the following embodiment, but may be altered in many variations within the scope of claims. That is, an embodiment based on a proper combination of technical method disclosed in different embodiments is encompassed in the technical scope of the invention.

[1] Definition of Terms (1-1) "Water Absorbent Resin"

"water absorbent resin" used herein is a water swellable and water insoluble polymer gellant. "water swellable property" indicates CRC (water absoption capacity without load) of the water absorbent resin, which is set forth in ERT 441.2-02, is essentially 5 g/g or more, preferably 10 to 100 g/g, and more preferably 20 to 80 g/g. "water insoluble property" indicates that Ext (water extractables) of a water absorbent resin, which are set forth in ERT 470.2-02, are essentially 0 to 50% by weight, preferably 0 to 30% by weight, still more preferably 0 to 20% by weight, and particularly preferably 0 to 10% by weight.

The water absorbent resin is not specifically limited, and it can be appropriately designed according to the use. Preferably, it is a hydrophilic crosslinked polymer obtained by crosslinking polymerization of an unsaturated monomer having a carboxy group. The water absorbent resin is not limited to an embodiment where whole amount (100%) is a polymer, and may include additives and the like, in an amount of the range to maintain the performance. Specifically, even a water absorbent resin composition is broadly referred to as a water absorbent resin in the invention. Content of the polyacrylic acid (salt)-type water absorbent resin is 70 to 99.9% by weight, more preferably 80 to 99.7% by weight, and still more preferably 90 to 99.5% by weight relative to the total amount. As components other than the water absorbent resin, in view of water absorbing speed or impact resistance of powders (particles), water is preferable and the additives to be described later are contained, as needed.

(1-2) "Polyacrylic Acid (Salt)"

In the present description, "polyacrylic acid (salt)" represents a polymer composed principally of acrylic acid and/or a salt thereof (herein below, referred to as acrylic acid (salt)) as a repeating unit in which a graft component is optionally included.

Specifically, it represents a polymer containing acrylic acid (salt) essentially in 50 to 100% by mole, preferably 70 to 100% by mole, more preferably 90 to 100% by mole, and particularly preferably substantially 100% by mole, in the entire monomers (excluding an internal crosslinking agent) used in polymerization. The salt as the polymer contains essentially a water soluble salt, when polyacrylic acid salt is used as a polymer. The polyacrylic acid salt as polymer essentially includes a water soluble salt, and the salt is preferably a monovalent salt, and further preferably an alkali metal salt or an ammonium salt, the alkali metal salt is more preferable, and further a sodium salt is particularly preferable.

(1-3) "EDANA" and "ERT"

"EDANA" is an abbreviation of European Disposables and Nonwovens Association, and "ERT" is an abbreviation of the measurement method (EDANA Recommended Test Methods) for the water absorbent resin of a European standard (nearly a world standard).

Meanwhile, in the present description, unless otherwise specified, the ERT original (which is a known literature revised in 2002) is referred to for measuring physical properties of the water absorbent resin.

(a) "CRC" (ERT 441.2-02)

"CRC" is an abbreviation of centrifuge retention capacity and it represents water absorption capacity without load (herein below also referred to as "water absorption capacity"). Specifically, it is an water absorption capacity (unit: [g/g]) at which 0.200 g of a water absorbent resin present in a non-woven fabric is freely swollen in a large excess amount of a 0.9 wt % sodium chloride aqueous solution for 30 minutes and further drained by centrifugation.

(b) "AAP" (ERT 442.2-02)

"AAP" is an abbreviation of absorption against pressure and it means water absorption capacity with load. In detail, AAP is an absorbency (unit: [g/g]) at which 0.200 g of a water absorbent resin placed under a pressure of 2.06 kPa (0.3 psi, 21 [g/cm$^2$]) is swollen in a 0.9 wt % sodium chloride aqueous solution for an hour. In the invention, the measurement was made with changing the pressure condition into a pressure of 4.83 kPa (0.7 psi, 50 [g/cm$^2$]) for one hour.

(c) "Ext" (ERT 470.2-02)

"EXT" is an abbreviation of extractables and represents water extractables in water (quantity of water soluble component). The extractables are of a value (unit: weight %) determined through steps of dissolving 1.000 g of a water absorbent resin in 200 g of a 0.9% by weight sodium chloride aqueous solution, stirring a mixture thereof for 16 hours, and measuring an amount of the polymer dissolved in the solution by pH titration.

(d) "FSC" (ERT 440.2-02)

"FSC" is an abbreviation of a free swell capacity. Specifically, FSC is a water absorption capacity (unit: [g/g]) at which 0.20 g of a water absorbent resin is immersed in a 0.9% by weight sodium chloride aqueous solution for 30 minutes, without draining by centrifugation.

(e) "Residual Monomers (ERT 410.2-02)"

"Residual monomers" indicate an amount of monomers that are remained in a water absorbent resin. Specifically, it is an amount (unit: ppm) obtained by adding 1.000 g of a water absorbent resin to 200 mL of 0.9% by weight sodium chloride aqueous solution, stirring for 2 hours, and then measuring the amount of residual monomer dissolved into the solution by high performance liquid chromatography.

(f) "PSD" (ETR 420.2-02)

"PSD" is an abbreviation of a particle size distribution and represents a particle size distribution determined by sieve classification. The weight average particle diameter (D50) and particle size distribution width are measured according to the same method as "(1) Median Particle Size and Distribution of Particle Size" described in lines 25 to 43 at page 7 of EP Patent No. 0 349240.

(g) Measurement of Other Physical Properties of Water Absorbent Resin Set Forth in EDANA "pH" (ERT 400.2-02):

It represents pH of a water absorbent resin.

"Moisture Content" (ERT 430.2-2):

It represents a moisture content in a water absorbent resin.

"Flow Rate" (ERT 450.2-02): It represents a flow rate of a water absorbent resin.

"Density" (ERT 460.2-02):

It represents a bulk density of a water absorbent resin.

"Respirable Particles" (ERT 480.2-02): It represents water absorbent resin powder in breathable region.

"Dust" (ERT 490.2-02):

It represents powder dust contained in a water absorbent resin.

(1-4) "Liquid Permeability"

"liquid permeability" represents flow of liquid that flows among particles of water absorbent resin powder swelled with load or without load. A typical measurement method of "liquid permeability" includes SFC (Saline Flow Conductivity) or GBP (Gel Bed Permeability).

The phrase "SFC (Saline Flow Conductivity)" represents a liquid permeability of 0.69% by weight of sodium chloride aqueous solution for 0.9 g of a water absorbent resin powder with load of 0.3 psi. SFC is measured by SFC testing method described in the specification of U.S. Pat. No. 5,669,894.

The phrase "GBP" represents a liquid permeability of 0.69% by weight of sodium chloride aqueous solution for a water absorbent resin powder with load or in free expansion. GBP is measured by GBP testing method described in WO 2005/016393.

(1-5) "Color Hue"

In the invention, color hue of a water absorbent resin right after the production or color hue of a water absorbent resin right after the shipment to a user is referred to as initial color hue. In general, it is controlled for color hue before shipment from factory. Examples of the color hue measurement method include those described in WO 2009/005114 (for example, Lab values, YI values, WB values, and the like).

Change in color hue of a water absorbent resin which occurs during a long time storage or commercial distribution in unused state is referred to as color hue over time. Due to coloration of a water absorbent resin over time, product value of a disposable diaper may be lowered. The coloration over time occurs over several months to several years, and it is determined by acceleration test described in WO 2009/005114 (acceleration test under high temperature and high humidity).

(1-6) Others

The phrase "X to Y" indicating a range in the present specification represents "X or more and Y or less". The symbol "t (ton)" which is a unit of weight represents "Metric ton". The unit "ppm" represents "ppm by weight" or "ppm by mass" if not otherwise specified. In the present description "mass" and "weight", "% by mass" and "% by weight", and "parts by mass" and "parts by weight" have the same meaning as each other. Physical properties or the like are measured under the room temperature 20 to 25° C. and relative humidity of 40 to 50%, unless specifically described otherwise. The term "-acid (salt)" represents "-acid and/or a salt thereof", and the term "(meth)acryl" represents "acryl and/or methacryl".

[2] Method for Producing Water Absorbent Resin (2-1) Polymerization Step

This is a step for obtaining a crosslinked polymer in a hydrogel state (herein below, referred to as "hydrogel") by polymerization of an aqueous solution containing acrylic acid (salt) as a main component.

(a) Method for Producing Acrylic Acid

The method for producing acrylic acid, which is used as a raw material of the water absorbent resin provided by the invention, is not specifically limited. For example, the production method include a method of obtaining acrylic acid by vapor-phase oxidation of propylene or propane which is a fossil raw material and a method of obtaining acrylic acid by oxidation of glycerin or the like that is obtained from natural fats and oils as a non-fossil raw material. Such oxidations may be carried out via producing acrolein or may include isolating acrolein. Acrylic acid may be also obtained by direct oxidation.

Examples of method for producing a water absorbent resin by using acrylic acid derived from a non-fossil raw material are disclosed in WO 2006/092272, WO 2006/136336, WO 2008/023040, WO 2007/109128, and the like. Also, examples of the method for preparing acrylic acid from a non-fossil raw material are disclosed in WO 2006/087024, WO 2006/087023, WO 2007/119528, WO 2007/132926, US Patent Application Publication No. 2007/0,129,570, and the like.

(b) Impurities in Acrylic Acid

About the impurities contained in acrylic acid used in the invention, an amount of protoanemonin and/or furfural is preferably controlled so as to be a predetermined amount or less in consideration of a color hue stability or a residual monomer. The content thereof is preferably 0 to 10 ppm, more preferably 0 to 5 ppm, still more preferably 0 to 3 ppm, and particularly preferably 0 to 1 ppm.

For the same reason, it is preferable to include a smaller amount(s) of aldehydes other than furfural and/or maleic acid. An amount(s) thereof relative to acrylic acid is preferably 0 to 5 ppm, more preferably 0 to 3 ppm, still more preferably 0 to 1 ppm, and particularly preferably of 0 ppm (below the detection limit). Examples of aldehydes other than furfural encompass benzaldehyde, acraldehyde, acetaldehyde, and the like.

From the view point of reducing a residual monomer, acrylic acid includes dimer acrylate in amount preferably 0 to 500 ppm, more preferably 0 to 200 ppm, and still more preferably 0 to 100 ppm.

(c) Monomers (Excluding a Crosslinking Agent)

The water absorbent resin provided by the invention preferably contains, as a main component, acrylic acid (salt) as a raw material (monomer). In other words, according to the invention, it is preferable that the unsaturated monomer contains acrylic acid as a main component and the water absorbent resin is a water absorbent resin based on polyacrylic acid (salt). Polymerization of the monomer is generally carried out in an aqueous solution. A concentration of the monomer in the aqueous monomer solution is generally 10 to 90% by weight, preferably 20 to 80% by weight, more preferably 30 to 70% by weight, still more preferably 35 to 65% by weight, and particularly preferably 40 to 60% by weight.

In the hydrogel obtained by polymerization of an aqueous solution, at least part of the acidic group of the polymer is preferably neutralized from the view point of water absorption performance. The neutralization may be carried out before, during, or after the polymerization of acrylic acid. From the view point of improving productivity, water absorption against pressure (AAP) and saline flow conductivity (SFC), or the like, it is preferable that the neutralization is carried out before the polymerization of acrylic acid. Specifically, neutralized acrylic acid (that is, partially neutralized acrylic acid salt) is preferably used as a monomer.

To obtain more significant effect of the invention, an aqueous solution of monomer is polymerized preferably in neutral or basic condition, more preferably in neutral condition. Neutralization rate is not specifically limited. However, specifically, relative to an acidic group, it is preferably 10 to 100% by mole, more preferably 30 to 95% by mole, still more preferably 50 to 90% by mole, and particularly preferably 60 to 80% by mole. When the neutralization rate is less than 10% by mole, a CRC (water absorption capacity without load) may be lowered, in particular.

As below described in the section (i) Polymerization initiator, the salt dissociation rate of persulfate salt depends on pH of an aqueous solution of monomer and the rate decreases in order of "alkali, acidic, and neutral", and therefore the invention is preferably applied to a case that a neutralized type monomer is used, in which more persulfate salts are remained after polymerization, and in particular to a case that a neutral aqueous solution of monomer is polymerized.

When an acrylic acid (salt) is used in the invention as a main component, a hydrophilic or hydrophobic unsaturated monomer other than the acrylic acid (salt) (herein below, also referred to as "other monomer") may be used. Examples of the other monomer usable in the invention, not specifically limited, encompass methacrylic acid, (anhydrous) maleic acid, 2-(meth)acrylamide-2-methylpropanesulfonic acid, (meth)acryloxy alkane sulfonic acid, N-vinyl-2-pyrrolidone, N-vinyl acetamide, (meth)acrylamide, N-isopropyl(meth) acrylamide, N,N-dimethyl(meth)acrylamide, 2-hydroxyethyl(meth)acrylate, methoxypolyethylene glycol(meth) acrylate, polyethylene glycol(meth)acrylate, stearyl acrylate, and salts thereof, or the like. When such other monomer is used, the using amount thereof is not specifically limited as long as the water absorption characteristics of the water absorbent resin are not impaired. Preferably, it is 50% by weight or less, and more preferably 20% by weight or less relative to the total weight of the monomers.

(d) Neutralization Salt

The basic material used for neutralization of acrylic acid as a monomer or the polymer after polymerization (hydrogel) is not specifically limited, and preferred examples thereof include a monovalent basic material such as hydroxide of an alkali metal like sodium hydroxide, potassium hydroxide, and lithium hydroxide or a (hydrogen) carbonate salt like sodium (hydrogen) carbonate and potassium (hydrogen) carbonate. Sodium hydroxide is particularly preferable. The temperature or neutralization (neutralization temperature) is not specifically limited, but it is preferably 10 to 100° C., and more preferably 30 to 90° C. With regard to the conditions other than the condition for neutralization treatment or the like described above, conditions or the like described in WO 2004/085496 are preferably employed for the invention.

(e) Crosslinking Agent (Internal Crosslinking Agent)

In the invention, it is particularly preferable, in view of water absorption performance of the water absorbent resin obtained, to use a crosslinking agent (also referred to as an internal crosslinking agent). The internal crosslinking agent that can be used is not specifically limited, and examples thereof include a crosslinking agent which is polymerizable with acrylic acid, a crosslinking agent which is reactive to a carboxyl group, and a crosslinking agent including both of them, or the like. Specific examples of the polymerizable crosslinking agent encompass a compound having at least two polymerizable double bonds within a molecule, such as N,N'-methylene bisacrylamide, (poly)ethylene glycol di(meth)acrylate, (polyoxyethylene)trimethylol propane tri(meth)acrylate, and poly(meth)allyloxyalkane. Examples of the reactive crosslinking agent encompass: a covalent crosslinking agent such as polyglycidyl ether such as ethylene glycol diglycidyl ether, polyalcohol such as propanediol, glycerin, sorbitol; and an ionic bonding crosslinking agent, which is a polyvalent metal compound such as aluminum. Of these, in view of a water absorption performance, it is preferable to use the crosslinking agent which is polymerizable with acrylic acid. Particularly, it is preferable to use an acrylate-type polymerizable crosslinking agent, an allyl-type polymerizable crosslinking agent, and an acrylamide-type polymerizable crosslinking agent. The internal crosslinking agent may be used either singly or in combination of two or more. In consideration of physical properties, the using amount of the internal crosslinking agent relative to the monomer excluding the crosslinking agent is preferably 0.001 to 5% by mole, more preferably 0.005 to 2% by mole, still more preferably 0.01 to 1% by mole, and particularly preferably 0.03 to 0.5% by mole.

(f) Methoxy Phenols

According to the invention, from the view point of polymerization stability, methoxy phenols are preferably contained in the monomer. More preferably, p-methoxy phenol is contained therein. The content of the methoxy phenols is preferably 1 to 250 ppm, more preferably 5 to 200 ppm, still more preferably 10 to 160 ppm, and particularly preferably 20 to 100 ppm relative to the monomer (acrylic acid).

(g) Iron Component

In the invention, from the view point of coloration and polymerization rate of the water absorbent resin, it is preferable that iron ion is contained as iron component in the monomer or the aqueous solution of the monomer. Content of the iron ion is, in terms of $Fe_2O_3$, preferably 0 to 10 ppm, more preferably 0 to 5 ppm, still more preferably greater than 0 but less than 5 ppm, further still more preferably 0.001 ppm or more and less than 5 ppm, particularly preferably 0.001 to 4 ppm, and most preferably 0.005 to 3 ppm relative to the monomer. The content of iron ion can be controlled according to the method described in WO 2006/109842. The expression "in terms of $Fe_2O_3$" represents the correction of measured Fe (molecular weight: 55.845) into $Fe_2O_3$ (molecular weight: 159.69), irrespective of the counter ions for Fe.

When the content of iron ion is not within the range described above, there is a possibility that coloration of the water absorbent resin occurs. Also, in the case where the content of iron ion is set to N. D (the detection limit or less, 0 ppm), there is a risk that causes an increase in cost, yielding the effect not worth the cost, and slowing down a polymerization rate in a case of a redox polymerization or the like.

Meanwhile, the amount of iron in the water absorbent resin can be measured, for example, by an ICP emission spectrophotometry set forth in JIS K1200-6. Regarding an ICP emission spectrophotometry instrument, ULTIMA manufactured by Horiba, Ltd. and the like are commercially available.

(h) Other Components in Aqueous Solution of Monomer

In order to improve various physical properties of the water absorbent resin obtained by the invention, the following materials can be added as an optional component to the aqueous solution of a monomer. Specifically, starch or a water soluble resin or water absorbent resin such as polyacrylic acids (salt), polyvinyl alcohol, and polyethylene imine or the like may be added in an amount of 0 to 50% by weight, preferably 0 to 20% by weight, more preferably 0 to 10% by weight, and still more preferably 0 to 3% by weight relative to the monomer. Additive such as various foaming agents (carbonate salt, azo compound, air bubbles, or the like), a surfactant, various chelating agents, hydroxy carboxylic acid, or a reductive inorganic salt may be added in an amount of 0 to 5% by weight, and preferably 0 to 1% by weight relative to the monomer, for example.

Among them, when preventing coloration of the water absorbent resin over time or improving urine resistance (preventing gel deterioration) is desired, chelating agent, hydroxy carboxylic acid, or reductive inorganic salt is preferably used. The chelating agent is particularly preferably used. The using amount for such case is preferably 10 to 5000 ppm, more preferably 10 to 1000 ppm, still more preferably 50 to 1000 ppm, and particularly preferably 100 to 1000 ppm relative to the water absorbent resin. As for the chelating agent, hydroxy carboxylic acid, or reductive inorganic salt, the compounds described in WO 2009/005114, EP Patent No. 2 057 228, or EP Patent No. 1 848 758 can be used.

(i) Polymerization Initiator

A polymerization initiator for use in the invention is selected as needed in accordance with the polymerization type. Although not specifically limited, it may contain water soluble peroxides as a radical polymerization initiator. Examples of the water soluble peroxides as a radical polymerization initiator include persulfate salts such as sodium persulfate, potassium persulfate, and ammonium persulfate; and, peroxides like hydrogen peroxide, t-butyl peroxide, and methyl ethyl ketone peroxide. Of these, persulfate salt is preferably used. More preferably, potassium persulfate (half life ($\tau$) at 90° C.: 1.24 hours) or ammonium persulfate (half life ($\tau$) at 90° C.: 0.44 hours) are used. Still more preferably, sodium persulfate (half life ($\tau$) at 90° C.: 1.24 hours) is used.

The half life depends on pH and temperature of the solution. With regard to pH, the half time tends to increase in order of "alkali, acidic, and neutral". With regard to temperature, the half time tends to increase in order of "high temperature and low temperature". According to the invention, if sodium acrylate is used as a monomer of the water absorbent resin and a small amount of persulfate salt is used as a polymerization initiator preferably within the range described below, it substantially changes into sodium persulfate regardless of salt type. As such, based on the salt type of monomer, polymerization temperature, and polymerization time, remain time of persulfate salt as a polymerization initiator can be expected to an extent.

Sodium persulfate or potassium persulfate, for example, has half life ($\tau$) of 2100 hours (30° C.), 499 hours (40° C.), 130 hours (50° C.), 36.5 hours (60° C.), 11.1 hours (70° C.), 3.59 hours (80° C.), 1.24 hours (90° C.), or 0.45 hours (100° C.)

Inventors of the invention found that, because of productivity increase of a water absorbent resin accompanied with shortened polymerization time and increased amount of a polymerization initiator, more persulfate salt remains in hydrogel after polymerization and such residual persulfate salts in hydrogel before drying is a material causing deterioration of physical properties of a water absorbent resin and such problem is particularly significant at high concentration like 45% by weight or more. The invention was completed based on such findings. The polymerization time suitable for the invention is within the range described in the section of (j) Polymerization method, but it is not specifically limited thereto.

Use of water soluble peroxides as a radical polymerization initiator in combination with other initiator is also encompassed in the preferred embodiment of the invention. Examples thereof include azo compound such as 2,2'-azobis(2-amidino-propane)dihydrochloride and 2,2'-azobis[2-(2-imidazoline-2-yl)propane] dihydrochloride and photodegradable polymerization initiator such as benzoin derivative, benzyl derivative, acetophenone derivative, benzophenone derivative, and azo compound. An example of the redox-type polymerization initiator encompasses use of a reducing compound such as L-ascorbic acid or sodium bisulfite in combination with the persulfate or the peroxide.

In addition, the polymerization may be carried out by irradiation of activated energy rays such as radiation rays, electron beams, and UV rays to the aqueous solution of monomer. And, the polymerization may be carried out by the use of water soluble peroxides as a radical polymerization initiator in combination with the activated energy rays.

Using amount of the polymerization initiator (in particular, using amount of persulfate salt) relative to the monomer is preferably 0.0001 to 1% by mole, more preferably 0.001 to 0.5% by mole, still more preferably 0.01 to 0.3% by mole, and particularly preferably 0.03 to 0.2% by mole. Use of the polymerization initiator in an amount of 1% by mole or less can suppress the coloration of the water absorbent resin, whereas use of the polymerization initiator in an amount of 0.0001% by mole or more may reduce residual monomers. When a polymerization initiator other than persulfate salt is used in combination with persulfate salt, the ratio of the persulfate in the entire polymerization initiators within the above range is preferably 25% by mole or more, more preferably 50% by mole or more, and still more preferably 75% by mole or more.

According to the invention, from the view point of reducing residual monomers or production cost, water soluble peroxides are used as a polymerization initiator. In particular, persulfate salt is used, and the using amount is 100 ppm or more, preferably 200 ppm or more, more preferably 300 ppm or more, and still more preferably 400 ppm or more relative to the total amount of the monomer (unsaturated monomer). The upper limit is 10000 ppm.

(j) Polymerization Method

According to the invention, in consideration of obtained water absorption performance of the water absorbent resin or an easiness of control of polymerization, or the like, when polymerizing an aqueous solution of a monomer, the polymerization step is generally carried out by aqueous polymerization or reverse phase suspension polymerization. Preferably, the aqueous polymerization is used. More preferably, continuous aqueous polymerization is used. In particular, it is preferably used for huge scale production which allows a great production amount of the water absorbent resin per line. The production amount is preferably 0.5 [t/hr] or more, more preferably 1 [t/hr] or more, still more preferably 5 [t/hr] or more, and particularly preferably 10 [t/hr] or more. Further, preferred examples of the aqueous solution polymerization encompass continuous belt polymerization (disclosed in U.S. Pat. Nos. 4,893,999, 6,241,928, and US Patent Application No. 2005/215,734 and others), and continuous kneader polymerization and batch kneader polymerization (disclosed in U.S. Pat. Nos. 6,987,151 and 6,710,141 and others) and others. Of these, the continuous kneader polymerization or continuous belt polymerization which increase solid components during polymerization particularly increase by 1% by weight more is preferable from the view point of cooperation with continuous drying as well as physical properties. The continuous belt polymerization is particularly preferable.

The polymerization time (it is defined as the time from the start of polymerization till discharge from the polymerization reactor) is appropriately determined, but is preferably 3 hours or less, and preferably in the order of 1 hour or less, 0.5 hours or less, and 0.2 hours or less. 0.1 hours or less is particularly preferable. Shorter the polymerization time is, better the effect of the invention is exhibited. As such, the invention can be more preferably applied to a polymerization condition which allows persulfate salt to remain. Although the lower limit of the polymerization time is suitably determined, from the view point of reducing residual monomers or the like, it is preferably 1 second or more, more preferably 0.5 minutes or more, and still more preferably 1 minute or more.

According to the invention, the rate of polymerization is preferably 60% by mole or more, and preferably in the order of 80% by mole or more, 90% by mole or more, and 95% by mole or more. The upper limit is 100% by mole. However, in the case of the rate of polymerization is 100% by mole, a long time may be required for the polymerization. Thus, from the view point of productivity, it is 99.9% by mole or so, or further 99% by mole or so.

Preferable example of the continuous aqueous polymerization encompasses high-temperature-starting polymerization, in which the polymerization initiation temperature is preferably 30° C. or more, more preferably 35° C. or more, still more preferably 40° C. or more, and particularly preferably 50° C. or more (an upper limit of the temperature of the monomer is a boiling point), and high-monomer-concentration-using polymerization, in which the concentration of monomer is preferably 35% by weight or more, more preferably 40% by weight or more, still more preferably 45% by weight or more (an upper limit of the concentration of the monomer is a saturated concentration). The polymerization initiation temperature is defined as the temperature of the liquid right before supplying the aqueous solution of a monomer to a polymerization reactor. However, the conditions or the like described in U.S. Pat. Nos. 6,906,159, 7,091,253, or the like may be suitably applied for the invention.

Further according to the invention, from the view point of improving the physical properties and drying efficiency of the water absorbent resin obtained in the invention, moisture is preferably vaporized during the polymerization. In other words, it is preferred in the polymerization of the invention that a hydrogel with high concentration of solid content is obtained. The level of increased solid content concentration ("concentration of solid content in the hydrogel after polymerization"-"concentration of monomer before polymerization") is preferably 1% by weight or more, more preferably 2 to 40% by weight, and still more preferably 3 to 30% by weight. In this regard, the solid content concentration in the hydrogel obtained is preferably 80% by weight or less.

These polymerizations can be carried out in an air atmosphere. However, in view of the prevention of the coloration, it is preferable to carry out the polymerization in an inert gas atmosphere such as nitrogen or argon (for example, oxygen concentration is 1% by volume or less), and to polymerize a monomer component after replacing, by an inert gas, oxygen dissolved in the solution containing the monomer (for example, the dissolved oxygen concentration less than 1 [mg/L]). It may be carried out under reduced pressure, atmospheric pressure, or increased pressure. If necessary, the hydrogel obtained after the polymerization may be stored (aged) for reducing the residual monomers or controlling the recycle time and others for continuous production, after discharged from the polymerization reactor.

(2-2) Gel Micronization Step (Gel Crushing Step)

This is a step of crushing the hydrogel obtained from the polymerization step described above and followed by storing (aging) as required, to obtain particulate hydrogel (herein below, referred to as "particulate hydrogel").

The hydrogel obtained from the above polymerization step may be subjected to drying as it is. However, to solve the problems, the hydrogel may be gel-crushed, preferably during or after the polymerization, by using a crushing machine (kneader, meat chopper, cutter mill, or the like) as needed to yield particulates. Specifically, between the polymerization step using continuous belt polymerization or continuous kneader polymerization and the drying step, the hydrogel micronization step (herein below, also referred to as "gel crushing") may be further included. Even when the gel is micronized by dispersion in a solvent during polymerization such as reverse phase suspension polymerization, that case is regarded to be encompassed by the micronization (micronization of the polymerization step) of the invention. However, it is preferably crushed by using a crushing machine.

In view of physical properties, temperature of the hydrogel to be gel crushed is kept or heated preferably 40 to 95° C. and more preferably 50 to 80° C. A resin solid content (solid content concentration) of the particulate hydrogel either during or after the gel crushing is not particularly limited. However, in view of the physical properties, it is preferably 45% by weight or more, more preferably 45 to 80% by weight, and preferably 55 to 80% by weight. The range described in the following section (2-3) is still more preferable. Under the purpose of enhancing the crushing efficiency, water, polyhydric alcohol, a mixture solution of water and polyhydric alcohol, a aqueous solution of polyvalent metal, vapors thereof, or the like may be added as necessary during the gel crushing step. When the hydrogel having high solid content concentration (for example, 45 to 80% by weight as described above) to which the invention can be preferably applied is crushed, the inside of a crushing machine can be circulated with air, preferably with dry air.

The weight average particle diameter (D50) of the particulate hydrogel after gel crushing is preferably 0.2 to 4 mm, more preferably 0.3 to 3 mm, and still more preferably 0.5 to 2 mm from the view point of controlling the drop and scatter ratio at low level. By controlling the weight average particle diameter (D50) of the particulate hydrogel within the range described above, the drying is efficiently carried out, and therefore desirable. The ratio of the particulate hydrogel having a particle size of 5 mm or more is preferably 0 to 10% by weight, and more preferably 0 to 5% by weight relative to the entire particulate hydrogel.

Meanwhile, the particle size of the particulate hydrogel is obtained by classifying with a sieve with a specific hole size, similar to the particle size of the water absorbent resin after the crushing step. The weight average particle diameter (D50) can be obtained in a same manner. However, when dry-type classifying operation of the particulate hydrogel is difficult to achieve due to aggregation or the like, the wet classifying method described in paragraph [0091] of JP-A No. 2000-63527 can be used for the measurement.

Since the micronization of hydrogel is generally performed for a short time (for example, within 10 minutes or further within 1 minute) at the above temperature, in consideration of the half life of persulfate salt (for example, half life ($\tau$) of sodium persulfate at 90° C.; 1.24 hours), the particulate hydrogel is dried in a state in which persulfate salt is present in almost the same amount as the persulfate salt remained in hydrogel after the polymerization.

(2-3) Drying Step

The invention is characterized by the drying step as described below. Specifically, the invention is characterized in that, with regard to a method for producing a water absorbent resin by drying particulate hydrogel with high solid content concentration (45% by weight or more), peroxide (water soluble peroxide, in particular persulfate salt) remaining in the hydrogel is controlled to 100 ppm or less when hot air drying is carried out at high temperature (160° C. or more) as a drying method. By such drying step, deterioration of physical properties of hydrogel can be suppressed, and in particular, a water absorbent resin having low water extractables and improved liquid permeability can be obtained.

(a) Solid Content Concentration in Hydrogel

Herein, the solid content concentration in particulate hydrogel is 45% by weight or more, further in order of 50% by weight or more, 55% by weight or more, and 60% by weight or more. The upper limit is, although not specifically limited as long as it is a hydrogel, 80% by weight or less, further 75% by weight or less, and particularly 70% by weight or less. When the solid content concentration is less than 45% by weight, not only the productivity is low but also the characteristic effect of the invention is not easily exhibited. On the other hand, when the solid content concentration is excessively high, physical properties like water absorption capacity may be impaired. The solid content concentration in particulate hydrogel to be dried may be suitably determined within the upper and lower limit described above, depending on desired physical properties or productivity. It is preferred in an order of 45 to 80% by weight, 45 to 75% by weight, 50 to 75% by weight, 55 to 80% by weight, 50 to 70% by weight, 55 to 70% by weight, and 60 to 70% by weight. The solid content concentration is determined depending on the concentration of monomer during polymerization or vaporization during polymerization as well as the additives that are added either during or after the polymerization as required. However, the solid content concentration may be also controlled by adding a water absorbing resin powder or a hydrogel thereof as an additive.

(b) Amount of Peroxides

The invention is characterized in that, during the drying step, the amount of water soluble peroxide remaining in hydrogel is controlled to be low at the time of contacting with hot air of high temperature. More specifically, the invention is characterized in that, the amount of water soluble peroxides remaining in hydrogel at contacting with hot air of high temperature is controlled to be 100 ppm or less, preferably 95 ppm or less, and in the order of 90 ppm or less, 85 ppm or less, 80 ppm or less, 75 ppm or less, and 70 ppm or less relative to the solid content. As used herein, the hot air of high temperature indicates the temperature of 160° C. or more. Specifically, the drying step of the invention is characterized in that the amount of peroxides in the particulate hydrogel subjected to drying is 100 ppm or less relative to the weight of the solid content of the particulate hydrogel, and the drying temperature of the particulate hydrogel in the drying step is 160° C. or more. When the heating temperature is less than 160° C., the drying speed is lowered then the generation of non-dried products or lowered water absorption capacity caused by less amount of dried solid content may easily occur. However, if drying time is extended to avoid such problems, larger facilities are required. As such, the drying is carried out under the high temperature condition such as 160° C. or more, preferably 170° C. or more, and more preferably 180° C. or more. Meanwhile, the lower limit of the peroxides is, although not specifically limited, 1 ppm or more from the view point of lowering residual monomers.

It is conventionally known by the above patent literatures or the examples included therein that persulfate salt such as sodium persulfate is used as a polymerization initiator for polymerization of polyacrylic acid-type water absorbent resin. However, it is found by the inventors that most of the persulfate salt remains in hydrogel after polymerization. When persulfate salt is used for polymerization conventionally, hydrogel containing persulfate salt in an amount of several hundred ppm to several thousand ppm is supplied to the drying step. It was also found by the inventors that, drying of hydrogel which contains such large amount of persulfate salt, the physical properties are deteriorated, in particular, the physical properties are significantly deteriorated when hydrogel with solid content concentration of 45% by weight or more is dried at the temperature of 160° C. or more. Then, the content of the persulfate before drying is controlled when hydrogel with solid content concentration of 45% by weight or more is dried, and the invention is completed accordingly.

Recently, in accordance with increased production amount of a water absorbent resin, there is a tendency that polymerization time is shortened under the purpose of making a progress in polymerization technique and improving productivity (in particular, within 3 hours, and more preferably in the order of within 1 hour, within 0.5 hours, within 0.2 hours, and within 0.1 hours). As a result of shortening the polymerization time (or increasing the amount of polymerization initiator for improving productivity), more persulfate salt (for example, half life ($\tau$) at 90° C.; 1.24 hours for sodium persulfate) tends to remain in hydrogel after polymerization. There is also a problem that the physical properties of a water absorbent resin after drying are deteriorated by increasing the polymerization concentration for improving productivity (in particular, 45% by weight or more). To solve such problems, the inventors found that the persulfate salt contained in hydrogel is important for drying at temperature of 160° C. or more and concentration of 45% by weight and the critical point is present at 100 ppm, and as a result, completed the invention which is characterized in that the persulfate is controlled to be 100 ppm or less.

As described in the section (i) Polymerization initiator, sodium persulfate or potassium persulfate, for example, has half life ($\tau$) of 2100 hours (30° C.), 499 hours (40° C.), 130 hours (50° C.), 36.5 hours (60° C.), 11.1 hours (70° C.), 3.59 hours (80° C.), 1.24 hours (90° C.), or 0.45 hours (100° C.). It was found that the residual amount of a polymerization initiator increases due to the recent improvement in the productivity of a water absorbent resin (shortened polymerization time or increased amount of polymerization initiator) and the half life described above.

In Patent Literature 28, a method of drying at 100 to 250° C. and controlling index of thermally degradable radical polymerization initiator content in hydrogel before drying to be 40 to 100 is disclosed. In this regard, the expression "index of thermally degradable radical polymerization initiator content" indicates the value obtained by the following equation 1.

[Expression 1]

(Index of thermally degradable radical polymerization initiator content)=$(Ci/Mi)/(Cm/Mm)\times 10^5$ [Formula 1]

Ci: Amount of extracted thermally degradable radical polymerization initiator after stirring hydrogel right before drying step for 1 hour in 5% by weight of sodium chloride solution [unit: % by mass]

Mi: Molar average molecular weight of extracted thermally degradable radical polymerization initiator [unit: mol/g]

Cm: Amount of solid content of hydrogel after drying for 8 hours at 180° C. [unit: % by mass]

Mm: Molar average molecular weight of polymerized monomer [unit: mol/g]

Specifically, in the Table 1 of Patent Literature 28, as defined by the method of Patent Literature 28, it is disclosed that Cm in the Equation 1 is 40.7 to 41.4% by mass and Ci is 0.0504 to 0.0826% by mass (per amount of solid content, 1223 to 2005 ppm) in the Examples 1 to 5, and in the Comparative examples 1 to 4 it is disclosed that Cm is 40.8 to 41.4% by mass and Ci is 0.0319 to 0.0403% by mass (per amount of solid content, 782 to 934 ppm). In the Example 6 and 7 of the Table 4 of the same literature, it is disclosed that Cm is 50.75% by mass (the Example 6) and 51.02% by mass (the Example 7), Ci is 0.0698% by mass (per amount of solid content, 1375 ppm) (the Example 6) and 0.0851% by mass (per amount of solid content, 1667 ppm) (the Example 7). In the Comparative example 5, Cm is 50.35% by mass and Ci is 0.0495% by mass (per amount of solid content in terms of calculated value, about 983 ppm).

According to the technique disclosed in Patent Literature 28, a thermally degradable radical polymerization initiator such as persulfate salt is increased at the time of drying (Examples 1 to 7 of Patent Literature 28 (persulfate salt per amount of solid content; about 1233 to 2005 ppm)) compared to conventional technique or the Comparative examples 1 to 5 of Patent Literature 28 (persulfate salt per amount of solid content; about 782 to 983 ppm) so that the index of thermally degradable radical polymerization initiator content in hydrogel is set to 40 to 100. However, it has problems like coloration. For such reasons, unlike Patent Literature 28 or the like, the present invention lowers the persulfate salt to 100 ppm (per amount of solid content, 100 ppm) or less in a hydrogel at the time of drying the hydrogel which has a solid content concentration of 45% by weight or more, preferably 50% by weight or more, more preferably 55% by weight or more, and still more preferably 60% by weight or more, so that GEX (relationship between water absorption capacity and water extractables) or the like is further improved.

When the index of the thermally degradable radical polymerization initiator content of Patent Literature 28 is calculated with the condition that persulfate salt in hydrogel before drying is 100 ppm (upper limit in the invention) and solid content concentration is 70% by weight, it is found to be 7.5. Thus, according to the invention, when the solid content concentration is 45% by weight or more and far outside the region of Patent Literature 28 (40 to 100), and even when the hydrogel of the high concentration, which is not disclosed in Patent Literature 28 (for example 70% by weight of the Examples 1 to 4), is dried, the high physical properties (GEX value) can be maintained. Meanwhile, the solid content concentration that is suitable for the invention is the same as those described above.

As for the drying method, various methods including drying by heating, drying by hot air, drying under reduced pressure, drying by infrared ray, drying by microwave, drying using a drum dryer, drying based on azeotropic dehydration with a hydrophobic organic solvent, and drying under high humid condition by using high temperature water vapor or the like can be adopted.

Shape of the dried polymer is generally a particulate shape or an aggregate thereof (for example, block-shaped material; Patent Literature 1), but not specifically limited thereto. The aggregate obtained from drying step itself may be supplied to the crushing step. However, if necessary, it is disintegrated (de-aggregated) at an exit of a dryer to have again the particulate with the weight average particulate diameter (D50) of 0.1 to 10 mm, preferably 0.5 to 5 mm, and more preferably 1 to 3 mm, and then supplied to the next step, in particular, crushing step.

(c) Method for Reducing Amount of Peroxide

Method for reducing the amount of water soluble peroxide in the hydrogel is not specifically limited. Examples thereof include a method of performing the step for reducing peroxides before drying step, for example, (1) method of heating the particulate hydrogel crosslinked polymer at the temperature lower than 160° C. before drying step; and (2) the heating treatment of (1) is further carried out at an atmosphere with dew point of 50 to 100° C. or the like.

Specific condition for the above (1) includes setting the heating temperature (setting temperature or hot air temperature of dryer) at 80 to 150° C., preferably 80 to 140° C., more preferably 100 to 130° C., and still more preferably 100 to 120° C. Further, when a hot air dryer is used for the heating treatment, the direction of hot air may be either up-flow, down-flow, or parallel to the surface of the belt. In particular, it is preferable for the hot air that the first part of the drying step is run in up-flow direction while the latter part is run in down-flow direction to easily obtain an even state of particulate hydrogel. Heating time varies depending on the heating temperature and the using amount of the peroxides. In general, it is 1 minute to 1 hour, preferably 5 minutes to 1 hour, and more preferably 5 to 30 minutes. The drying step of the invention is preferably carried out after the method (1) or the method (2) for reducing peroxide. Although the method (1) may be less effective than the method (2) described below in terms of reducing the amount of residual monomers, the solid content concentration can be more easily increased compared to the method (2).

Specific conditions for the above (2) include that the heating temperature is set at 80 to 150° C., preferably 80 to 140° C., more preferably 100 to 130° C., and still more preferably 100 to 120° C. and the dew point inside the dryer is set at 50 to 100° C., and preferably 65 to 95° C. When a hot air dryer is used for the heating treatment, the direction of hot air may be either up-flow, down-flow, or parallel to the surface of the belt. In particular, it is preferable for the hot air that the first part of the drying step is run in up-flow direction while the latter part is run in down-flow direction to easily obtain an even state of particulate hydrogel. Heating time varies depending on the heating temperature and the using amount of the peroxides. In general, it is 1 minute to 1 hour, preferably 5 minutes to 1 hour, and still more preferably 5 to 30 minutes. The drying step of the invention is preferably carried out after the method (1). The method (2) is advantageous in that, compared to the method (1), time required for reducing peroxides is shortened and the residual monomers can be reduced at the same time.

The step for reducing peroxide may be carried out by using the same dryer as the dryer used for drying step described below or a separate dryer. Preferred embodiment includes, for example, with use of a continuous through-circulation belt dryer having a multi-chamber structure, setting the first chamber to have a treatment condition for the step for reducing peroxides and setting the second chamber (depending on each case, third chamber, fourth chamber, and so on) to have a condition for the drying step, and carrying out continuously the step for reducing peroxide and the drying step.

When the using amount of peroxides is more than 100 ppm relative to the monomer in the polymerization step and the residual amount of the peroxide is more than 100 ppm after polymerization, it is necessary to control the peroxide amount in the hydrogel provided to the drying step to 100 ppm or less by the step for reducing peroxide described above. A method for polymerization of a water absorbent resin by using a peroxide, in particular persulfate salts, is conventionally known from the U.S. patent described in (j) above or Patent Literatures 1 to 27 and others. According to the study by the inventors, it was found that most peroxides (in particular, persulfate salt) which were used in polymerization and remained in the hydrogel after polymerization (residual ratio of peroxide (in particular, persulfate salt) after polymerization varies depending on polymerization condition, but generally is 80% or more, or further 90% or more) and the residual peroxide (in particular, persulfate salt) affected on physical properties after drying or liquid permeability or the like after crosslinking. Control of peroxide in hydrogel and a control method are found, and the invention is completed accordingly.

(d) Drying Temperature for Drying Step

The drying temperature (defined as a temperature of the heating medium, in particular, temperature of hot air) for the drying step of the invention is 160° C. or more, preferably 160 to 200° C., and more preferably 170 to 190° C. By drying the particulate hydrogel at the drying temperature of 160° C. or more, shortening the time required for drying and reducing coloration of the dried product can be both achieved. The drying temperature is defined as a temperature of the heating medium used when direct heating based on thermal conduction is performed by using oil or vapor as a heating medium (for example, a drum dryer or the like). When the material is indirectly heated by a heating medium such as an oil or vapor with an air or the like intervening (for example, a through-circulation band dryer or the like), it is defined as the atmospheric temperature. When drying is carried out without using a heating medium, for example, irradiation of electronic beam or the like, it is defined as the temperature of the material (hydrogel polymer under drying).

(e) Drying Time During Drying Step

The drying time varies depending on the surface area of particulate hydrogel, the water content ratio, and the type of dryer, and it is suitably selected so as to obtain a desired water content ratio. For example, it is 10 to 120 minutes, and preferably 20 to 60 minutes. The dried product obtained by drying a hydrogel crosslinked polymer during the drying step is pulverized and subjected to size classification thereafter.

(f) Dew Point During Drying Step

The dew point of gas which is brought into contact with a hydrogel crosslinked polymer during the drying step is, although not specifically limited, preferably less than 70° C., preferably −5 to less than 70° C., and particularly preferably 0 to 60° C. It is also preferable during the drying step that the dew point is increased first and then decreased. By controlling the dew point within this range, drying speed can be improved. Meanwhile, during the drying step of the invention, the particulate hydrogel is preferably contacted with water vapor-air mixture gas and/or water vapor-inert gas, or water vapor.

(g) Drying Apparatus for Drying Step

The drying apparatus (dryer) used in the invention is not specifically limited, and one or more of a thermal conduction type dryer, a radiative heat transfer type dryer, a hot air heat transfer type dryer, and a dielectric heating dryer or the like can be used. From the view point of drying speed, a hot air heat transfer type dryer (herein below, referred to as a "hot air dryer") is preferable. Examples of the hot air dryer include an through-circulation belt (band) type, a through-circulation circuit type, a vertically through-circulation type, a parallel flow belt (band) type, a through-circulation tunnel type, a through-circulation channel and stirring type, a fluidized bed type, an air flow type, and a spraying type or the like. From the view point of controlling physical properties or performing continuously the step for reducing peroxide and the drying step, an through-circulation belt type dryer is preferable. Although other dryer may be used in combination, drying is preferably carried out by using a through-circulation belt type dryer (belt type dryer) only.

When a hot air dryer is used as a dryer, in the drying temperature range of 170 to 230° C., air speed within a hot air dryer is controlled to 3.0 [m/sec] or less. In addition, the direction of hot air supplied to a belt may be preferably either up-flow, down-flow, or parallel, or a combination thereof. Among them, down-flow is preferable. In particular, it is preferable for the hot air that the first part of the drying step is run in up-flow direction while the latter part is run in down-flow direction to easily achieve uniform drying.

Large scale continuous drying using an through-circulation belt type dryer in which an through-circulation belt length is 5 to 100 m, further 10 to 70 m, and particularly 20 to 60 m can be suitably used. For such case, the width of a through-circulation belt is, although not specifically limited, properly determined, generally, within the range of 0.5 to 10 m, and further 1 to 5 m. Ratio between the width direction and the length direction can be determined depending on the purpose. However, it is longer in the longitudinal direction compared to the width direction, that is, typically 3 to 500 times, and further 5 to 100 times.

When a through-circulation belt type dryer is used, examples of the through-circulation belt include a wire mesh (for example, sieve mesh size of 1000 to 45 μm) or a punching metal. Preferably, a punching metal is used. Examples of the shape of the hole of a punching metal can be broadly selected, and examples thereof include round hole, oval hole, rectangular hole, hexagonal hole, long and round hole, long rectangular hole, diamond-shape hole, cross-shape hole, and a combination thereof. The hole arrangement may be either a staggered shape or a parallel shape. The holes may be formed in three dimension like a louver (a bay window). Preferably, however, it has a hole in plane structure. The pitch direction may be either vertical or horizontal to the moving direction of a belt. It may be also either tilted or combination of any directions can be used. The hole size of the punching metal and the hole area ratio are described below.

(h) Conventional Drying Method

Conventionally, many methods for improving liquid permeability have been suggested like those of Patent Literatures 1 to 27. However, none of them has focused on the amount of persulfate salt. The inventors of the invention found that the solid content concentration, amount of persulfate salts in hydrogel, and heating temperature play a role in drying step at high concentration (45% by weight or more), and completed the invention accordingly. None of Patent Literatures 1 to 27 suggests the invention.

(2-4) Pulverization Step and Size Classification Step

It is a step for pulverizing and classifying the dried product obtained from the drying step above to yield a water absorbent resin.

According to this step, the dried product obtained from the above drying step may be used as it is as dry powder. However, it is preferable to adjust the particle size to a specific value in order to improve a physical property in surface crosslinking step described below. The adjustment of the particle size is not limited to the pulverization step or size classification step, and it may be carried out in polymerization (particularly the reverse phase suspension polymerization), collection of fine powder, granulation, or the like. In the description discussed hereinafter, the particle size is defined by a standard sieve (JIS Z8801-1 (2000)).

The pulverizer which may be used for the pulverization step is not specifically limited and any conventionally known pulverizer may be used. Specific examples thereof include roll mill, hammer mill, roll granulator, jaw crusher, gyratory crusher, cone crusher, roll crusher, and cutter mill, or the like. Of these, from the view point of size control, multi-level roll mill or roll granulator is preferably used.

For size classification step, various size classifying apparatuses based on sieve classification or air stream classification or the like may be used. When the surface crosslinking is performed as described below, the size classification step (the first size classification step) is preferably performed before the surface crosslinking step. Still more preferably, an additional size classification step is performed after the surface crosslinking step (the second size classification step).

From the view point of improving the physical properties of the water absorbent resin obtained from this step, the particle size is preferably adjusted so as to make the particle size be as follows. Specifically, the weight average particle diameter (D50) of the water absorbent resin before the surface crosslinking is preferably 200 to 600 μm, more preferably 200 to 550 μm, still more preferably 250 to 500 μm, and particularly preferably 350 to 450 μm. It is preferable that the ratio of fine particles which can pass through a sieve with sieve mesh size of 150 μm (JIS standard sieve) is preferably 0 to 5% by weight, more preferably 0 to 3% by weight, and still more preferably 0 to 1% by weight relative to the entire water absorbent resin. It is preferable that the ratio of large particles which may not pass through a sieve with sieve mesh size of 850 μm (JIS standard sieve) is preferably 0 to 5% by weight, more preferably 0 to 3% by weight, and still more preferably 0 to 1% by weight relative to the entire water absorbent resin. A logarithmic standard deviation (σζ) of particle size distribution of the water absorbent resin is preferably 0.20 to 0.40, more preferably 0.25 to 0.37, and still more preferably 0.25 to 0.35. Such particle size may also be applied to the water absorbent resin after surface crosslinking or the water absorbent resin as a final product. If necessary, a size classification (i.e., second size classification) or a granulation step may be included even after the surface crosslinking for adjustment of particle size. The particle size may be defined by standard sieve classification, and it is measured by the method disclosed, in EDANA-ERT 420.2-02 (particle size distribution) with reference to the method of WO 2004/69915 (weight average particle diameter, σζ).

Generally when the water absorbent resin is controlled to have narrow particle size distribution, that is, it is controlled to have a small difference between the upper limit and lower limit of the particle size, coloration of a water absorbent resin is significant when measuring color hue. However, no such problem in color hue is found in the invention, and therefore desirable. Thus, for the particle size distribution of the water absorbent resin obtained by the invention, the ratio having particle size of 150 to 850 μm is 95% by weight or more, and preferably 98% by weight or more (upper limit is 100% by weight).

(2-5) Surface Crosslinking Step

According to the invention, for improving the absorption performance, it is preferable that a surface crosslinking step which can crosslink the surface of the dried water absorbent resin obtained from the drying step is further contained. By undergoing the surface crosslinking step, the water absorbent resin with an improved saline flow conductivity (SFC) (SFC is 10 [×$10^{-7}$·cm$^3$·s·g$^1$] or more) can be obtained. Herein below, preferred mode of the surface crosslinking step of the invention is described.

In the invention, a covalent surface crosslinking agent is used. Preferably, a covalent surface crosslinking agent and an ionic bonding surface crosslinking agent are used in combination. When a covalent surface crosslinking agent and an ionic bonding surface crosslinking agent are used in combination, the covalent surface crosslinking agent and ionic bonding surface crosslinking agent may be simultaneously added to the reaction system, or they may be added in order. When they are added in order, the addition order is not specifically limited, and the covalent surface crosslinking agent may be added first and then the ionic bonding surface crosslinking agent is added, or the ionic bonding surface crosslinking agent may be added first and the ionic bonding surface crosslinking agent is added. When the covalent surface crosslinking agent and ionic bonding surface crosslinking agent are used in combination, the crosslinking reaction caused by covalent surface crosslinking agent and the crosslinking reaction caused by ionic bonding surface crosslinking agent may be carried out either simultaneously or separately.

(Covalent Surface Crosslinking Agent)

As a surface crosslinking agent that can be used in the invention, various organic crosslinking agents or inorganic crosslinking agents can be used. Among them, a covalent surface crosslinking agent (an organic surface crosslinking agent) is preferable. From the view point of physical properties, a covalent surface crosslinking agent is preferably used, and examples thereof include polyhydric alcohol compound, epoxy compound, polyvalent amine compound, or a condensate between these compounds and halo-epoxy compound; oxazoline compound, (mono, di, or poly) oxazolidinone compound, and an alkylene carbonate compound. In particular, dehydration reactive crosslinking agent including polyhydric alcohol compound, alkylene carbonate compound, and oxazolidinone compound which requires reaction at high temperature may be used. For the case that no dehydration reactive crosslinking agent is used, more specific examples thereof include the compounds exemplified in U.S. Pat. Nos. 6,228,930, 6,071,976, 6,254,990, or the like. For example, there are included polyhydric alcohol compound such as mono, di, tri, or tetra-propylene glycol, 1,3-propanediol, glycerin, 1,4-butanediol, 1,3-butanediol, 1,5-pentanediol, 1,6-hexanediol, and sorbitol; epoxy compound such as ethylene glycol diglycidyl ether and glycidol; alkylene carbonate compound such as ethylene carbonate; oxetane compound; and cyclic urea compound such as 2-imidazolidinone; or the like.

Using amount of the surface crosslinking agent is appropriately selected as 0.001 to 10 parts by weight, and 0.01 to 5 parts by weight, relative to 100 parts by weight of the water absorbent resin. In addition to the surface crosslinking agent, water is preferably used. Amount of water for use in this case is 0.5 to 20 parts by weight, and more preferably 0.5 to 10 parts by weight, relative to 100 parts by weight of the water absorbent resin. When the covalent surface crosslinking agent and ionic bonding surface crosslinking agent are used in combination, each of them is used in an amount of the range described above.

In addition to water, a hydrophilic organic solvent with the surface crosslinking agent may be used in combination. The using amount thereof is 0 to 10 parts by weight, and preferably 0 to 5 parts by weight, relative to 100 parts by weight of the water absorbent resin particles.

Within the range the effect of the invention is not impaired, for example, 0 to 10 parts by weight or less, preferably from 0 to 5 parts by weight, and more preferably 0 to 1 part by weight, water insoluble fine particle powder or a surfactant may be also present at the time of mixing the crosslinking solution with the water absorbent resin particles. The using surfactants and the amount thereof are exemplified in U.S. Pat. No. 7,473,739.

The water absorbent resin is preferably subjected to heat treatment after mixing with the surface crosslinking agent. After that, it is subjected to cooling treatment, if necessary. Heating temperature for the heat treatment is 70 to 300° C., preferably 120 to 250° C., and more preferably 150 to 250° C. The heating time for the heating treatment is preferably in the range of 1 minute to 2 hours. The heat treatment may be carried out by using a common dryer or heating furnace. The surface crosslinking methods that are described in EP Patent Nos. 0 349 240 B, 0 605 150 B, 0 450 923 B, 0 812 873 B, 0 450 924 B, 0 668 080 B, 1 770 113 B, Japanese Patent Application Laid-Open (JP-A) Nos. 7-242709, 7-224204, U.S. Pat. Nos. 5,409,771, 5,597,873, 5,385,983, 5,610,220, 5,633,316, 5,672,633, 5,462,972, WO 99/42494, WO 99/43720, and WO 99/42496 and others may be also applied to the invention. Coloration may occur according to the technique disclosed in EP Patent No. 1 770 113 B or the like in which persulfate salt is used for surface crosslinking after drying. According to the invention, however, such problem is avoided by controlling persulfate salt in an amount of 100 ppm or less before drying.

According to the invention, a water absorbent resin having extremely white color can be provided even under hot temperature heating or air (hot air) drying, which causes severe coloration according to conventional techniques.

When a hygiene material (in particular, disposable diaper) is desired, in particular, it is preferable that the absorbency against pressure (AAP) is increased to the range of described below, preferably 20 [g/g] or more, by surface crosslinking treatment.

(Ionic Bonding Surface Crosslinking Agent)

In addition to the organic surface crosslinking agent, an inorganic surface crosslinking agent, preferably aluminum cation, may be used to improve liquid permeability or the like. Examples of the inorganic surface crosslinking agent that can be used include salt (organic salts or inorganic salts) or hydroxide of a polyvalent metal, which is divalent or more, preferably tri- to tetravalent metal. Examples of the polyvalent metal that can be used include aluminum, zirconium or the like, and aluminum lactate, aluminum sulfate or the like can be also used. The inorganic surface crosslinking may be employed either simultaneously or separately from an organic surface crosslinking agent. Surface crosslinking by using polyvalent metal is disclosed in WO 2007/121937, WO 2008/092843, WO 2008/092842, U.S. Pat. Nos. 7,157,141, 6,605,673, 6,620,889, US Patent Application Publication Nos. 2005/0,288,182, 2005/0,070,671, 2007/0,106,013, and 2006/0,073,969. As described in the following examples, the surface crosslinking by using aluminum cation may be also referred to as an aluminum surface treatment.

The liquid permeability or the like may be also improved by further using polyamine polymer, in particular a polymer with weight average molecular weight of 5,000 to 1,000,000, either simultaneously or separately from the organic surface crosslinking agent. Examples of the polyamine polymer that can be used include those disclosed in U.S. Pat. No. 7,098,284, WO 2006/082188, WO 2006/082189, WO 2006/082197, WO 2006/111402, WO 2006/111403, and WO 2006/111404 and others.

As described above, by the surface crosslinking step after the drying step, liquid permeability (SFC) can be improved. When the water absorption capacity (CRC) after surface crosslinking is too high, SFC tends to decrease. As such, CRC is lowered by surface crosslinking until CRC is preferably 50 [g/g] or less, more preferably 45 [g/g] or less, still more preferably 40 [g/g] or less, and particularly preferably 35 [g/g] or less. For such case, CRC is lowered by surface crosslinking such that the CRC reduction ratio is 0.1 to 0.9 times, or further 0.5 to 0.85 times, particularly 0.6 to 0.8 times in terms of CRC after and before the surface crosslinking. The lower limit of CRC is within the above range, and it is 10 [g/g] or more, further 20 [g/g] or more, and 25 [g/g] or more.

(Conventional Method for Improving Liquid Permeability)

According to recently required high performance for a disposable diaper, which is a main application of water absorbent resin, various functions are also needed for the water absorbent resin. Specifically, instead of having simply high water absorption capacity, a variety of physical properties such as gel strength, water extractable content, absorption speed, absorbency against pressure, liquid permeability, particles size distribution, urea resistance, antibiotic property, impact resistance, powder fluidity, deodorant property, coloration resistance, and low dust are now required for the water absorbent resin. For such reasons, many suggestions have been made regarding various surface crosslinking techniques, additives, and modification of production step, or the like.

Among the physical properties described above, in accordance with increase of using amount of water absorbent resin in a disposable diaper (for example, 50% by weight or more), the liquid permeability is regarded as a more important factor in recent years. Then, a variety of method of improving or modifying the liquid permeability under load or liquid permeability without load such as SFC and GBP has been suggested.

Combination of plural parameters including liquid permeability has been suggested for the physical properties described above, and a method of determining impact resistance (FI) (U.S. Pat. No. 6,414,214), a method of determining absorption speed (FSR/Vortex) (U.S. Pat. No. 6,849,665), and a method of determining product of liquid dispersion performance (SFC) and core absorption amount after 60 minutes (DA60) (US Patent Application Publication No. 2008/125,533) are known.

As a method for improving liquid permeability like SFC and GBP, a technique of adding gypsum either before or during the polymerization (US Patent Application Publication No. 2007/293,617), a technique of adding a spacer (US Patent Application Publication No. 2002/0,128,618), a technique of using a nitrogen-containing polymer in which a protonatable nitrogen is contained in an amount of 5 to 17 [mol/kg] (US Patent Application Publication No. 2005/0,245,684), a technique of using polyamine and a polyvalent metal ion or polyvalent anion (WO 2006/082197), a technique of coating a water absorbent resin whose pH is less than 6 with polyamine (WO 2006/074816), and a technique of using polyammonium carbonate (WO 2006/082189) are known. A technique of using polyamine with the soluble amount of 3% by weight or a technique of determining withdrawing index (WI) or gel strength is known (WO 2008/025652, WO 2008/025656, and WO 2008/025655). To improve coloration and liquid permeability, a technique of using polyvalent metal salt after controlling methoxy phenol as a polymerization inhibitor during polymerization is also known (WO 2008/092843 and WO 2008/092842). A technique of polishing particles to control bulk density at high level is also known (U.S. Pat. No. 6,562,879).

Conventionally, many methods for improving liquid permeability have been suggested in Patent Literatures 28 to 46 and others. However, none of them has focused on the drying step. The invention is, however, based on the finding that a certain drying step, in particular, solid content concentration and amount of persulfate salt in hydrogel, contributes to the improvement of liquid permeability, and the invention is completed accordingly. In this regard, the invention is not suggested in any one of Patent Literatures 28 to 46 and others.

(2-6) Fine Powder Recycling Step

This step is a step for recycling fine powder (fine powder containing powder with particle size of 150 μm or less in an amount of 70% by weight of more) separated from the drying step and, if necessary, the crushing step or the size classification step, to the polymerization step or the drying step, either as it is or after hydrated, and a method disclosed in US Patent Application Publication No. 2006/247,351 or U.S. Pat. No. 6,228,930 can be applied. By recycling of fine powder, particle size of the water absorbent resin can be controlled and high solid content concentration can be easily achieved by adding the fine powder. As the water absorbent resin can be easily released from a through-circulation belt of a dryer after drying, and therefore it is desirable.

(2-7) Other Steps

In addition to the steps described above, a vaporized monomer recycling step, a granulating step, and a fine powder removing step may be included, if required. The additives such as chelating agent, hydroxy carboxylic acid, and reductive inorganic salt can be added as necessary, to any one or all of the steps described above so as to attain stability of the color that changes over time, prevention of deterioration in gel, or the like.

The surface treatment step using polyvalent metal salt is applied when high liquid permeability against pressure (SFC or GBP) is required. The method disclosed in U.S. Pat. No. 6,605,673 or 6,620,889 is employed depending on necessity.

[3] Physical Properties of Water Absorbent Resin

The water absorbent resin of the invention contains polyacrylic acid (salt)-type water absorbent resin as a main component, and in case of using it in hygienic products, particularly a disposable diaper, it is obtained by the polymerization or the surface crosslinking or the like described above. Regarding the water absorbent resin obtained thereby, among the physical properties of the following (3-1) through (3-7), preferably at least one physical property is controlled, more preferably two or more physical properties including AAP are controlled, and particularly preferably three or more physical properties are controlled. If the water absorbent resin does not satisfy each physical property described below, sufficient performance may not be obtained from high-concentration diaper containing a water absorbent resin at the concentration of 40% by weight or more.

(3-1) Initial Phase Color Hue

The water absorbent resin obtained by the invention is preferably white powder as it is used as a raw material for hygiene products like a disposable diaper. Thus, in a Hunter Lab color system measurement by spectrophotometric colorimeter, the water absorbent resin has a value "L" (lightness), as initial phase color hue, preferably 85 or more, more preferably 87 or more, and still more preferably 89 or more. And, value "a" is preferably −2 to 2, more preferably −1 to 1, still more preferably −0.5 to 1, and particularly preferably 0 to 1. Value "b" is preferably −5 to 10, more preferably −5 to 9, still more preferably −4 to 8, and particularly preferably −1 to 7. Although the upper limit of the value "L" is 100, when it is 85 or more, a problem related with color hue does not occur in hygiene products or the like. Also, the water absorbent resin of the invention has YI (Yellow Index) value of preferably not more than 10, preferably not more than 8, and more preferably not more than 6, and WB (white balance) value of preferably 70 or more, more preferably 75 or more, and still more preferably 77 or more.

The initial phase color hue indicates the color hue of a water absorbent resin after production, and it generally represents the color hue measured before factory shipment. However, if stored under condition including temperature of 30° C. or less and relative humidity of 50% RH, a color hue measured within a year from the production can be adopted as the color hue.

(3-2) CRC (Water Absorption Capacity without Load)

A CRC (water absorption capacity without load) of the water absorbent resin obtained by the invention is preferably 10 [g/g] or more, more preferably 20 [g/g] or more, still more preferably 25 [g/g] or more, and particularly preferably 30 [g/g] or more. The upper limit of CRC is, although not specifically limited, preferably 50 [g/g] or less, more preferably 45 [g/g] or less, and still more preferably 40 [g/g] or less in relation to FC described later. When CRC is less than 10 [g/g], an absorption amount of the water absorbent resin is low, and therefore it may not be appropriate to use it as an absorbent in hygiene products like a disposable diaper. On the other hand, when CRC is higher than 50 [g/g], SFC is not improved or, hygiene products having good liquid-absorption speed may not be obtained when the water absorbent resin is used as a water absorbent. CRC can be appropriately controlled by using the internal crosslinking agent or the surface crosslinking agent described above.

(3-3) AAP (Absorption Against Pressure)

In order to prevent leakage from a disposable diaper, AAP (absorption against pressure) of the water absorbent resin obtained by the invention is preferably 20 [g/g] or more, more preferably 22 [g/g] or more, and still more preferably 24 [g/g] or more against pressure of 1.9 kPa or still more preferably 4.8 kPa, in which the drying is a means to achieve it. In consideration of balance between AAP and other physical properties, the upper limit of AAP is set at 40 [g/g] or less, although not specifically limited thereto. When AAP is less than 20 [g/g] and such water absorbent resin is used as an absorbent core, it may be impossible to obtain hygiene products in which return of the liquid once absorbed (in general, it is also referred to as "re-wet") by applying a pressure to the absorbent core is small. The AAP may be appropriately controlled by using the surface crosslinking agent or particle size or the like mentioned above.

(3-4) SFC (Saline Flow Conductivity)

In order to prevent leakage from a disposable diaper, SFC (saline flow conductivity), as liquid permeability against pressure, of the water absorbent resin obtained by the invention is, preferably 1 $[\times 10^{-7} \cdot cm \cdot s \cdot g^{-1}]$ or more, more preferably 10 $[\times 10^{-7} \cdot cm \cdot s \cdot g^{-1}]$ or more, still more preferably 50 $[\times 10^{-7} \cdot cm \cdot s \cdot g^{-1}]$ or more, particularly preferably 70 $[\times 10^{-7} \cdot cm \cdot s \cdot g^{1}]$ or more, and most preferably 100 $[\times 10^{-7} \cdot cm \cdot s \cdot g^{-1}]$ or more, and the drying is a means to achieve it. The upper limit of SFC is, not specifically limited, preferably 3000 $[\times 10^{-7} \cdot cm \cdot s \cdot g^{-1}]$ or less, and more preferably 2000 $[\times 10^{-7} \cdot cm \cdot s \cdot g^{-1}]$ or less. When the SFC is higher than 3000 $[\times 10^{-7} \cdot cm \cdot s \cdot g^{-1}]$ and such absorbent resin is used for an absorbing articles such as a disposable diaper, liquid spill from an absorbing article may occur in such actual use. The SFC may be appropriately controlled according to the drying method or the like described above.

(3-5) Ext (Water Extractables)

Ext (water extractables) of the water absorbent resin obtained by the invention is preferably 35% by weight or less, more preferably 25% by weight or less, still more preferably 15% by weight or less, and particularly preferably 10% by weight or less. When the Ext is higher than 35% by weight, gel strength of the water absorbent resin obtained may be weak and liquid permeability may be lowered. When such an absorbent resin is used in an absorbing article such as a disposable diaper, it may be impossible to obtain a water absorbent resin in which return of the liquid once absorbed (i.e., re-wet) by applying a pressure to the absorbent core is small. Ext may be appropriately controlled by using an internal crosslinking agent or the like described above.

(3-6) Residual Monomers (Residual Monomers)

From the view point of safety, an amount of the residual monomers (residual monomers) of the water absorbent resin obtained by the invention is controlled to preferably 0 to 400 ppm, more preferably 0 to 300 ppm, and still more preferably 0 to 200 ppm. The residual monomers may be appropriately controlled according to the polymerization method or the like described above.

(3-7) GEX Value

GEX value of the water absorbent resin obtained by the invention is preferably 21 or more, more preferably 22 or more, and still more preferably 23 or more. Although CRC (water absorption capacity without load) and Ext (water extractables) of the water absorbent resin contradict each other, the larger GEX value is more preferred as an indicator describing their relative relationship. However, the upper limit is 100 or so.

(3-8) Particle Size

Particle size is adjusted to the same range as the particles size described in section (2-4) above.

(3-9) Water Absorbent Resin of the Invention

The water absorbent resin obtained by the production method of the invention is a novel water absorbent resin having little residual monomers, high liquid permeability (SFC), and little residual persulfate salts, that is obtained by controlling the surface crosslinking, the particle size, and the water absorption capacity (CRC).

Specifically, the novel water absorbent resin obtained by an example of the production method of the invention is polyacrylic acid (salt)-type water absorbent resin in which absorbency (CRC) is 5 [g/g] or more, residual monomer is 0 to 200 ppm, saline flow conductivity (SFC) is 100 [$\times 10^{-7} \cdot cm \cdot s \cdot g^{-1}$] or more, and peroxide amount is 1 ppm or less.

The water absorbent resin preferably has CRC, GEX, AAP, particle size, and the like that are within the ranges described above. It is surface crosslinked, and it is particularly preferably surface crosslinked with a covalent surface crosslinking agent and an ionic bonding surface crosslinking agent. In addition, content of p-methoxy phenol in the water absorbent resin is preferably 0 to 40 ppm, more preferably 0 to 30 ppm, and still more preferably 0 to 20 ppm. Fe content is the same as the range described above. Peroxide amount is still more preferably 0.5 ppm or less. It is particularly preferably N.D. In the novel water absorbent resin of the invention, the residual monomer or persulfate salt is small and preferably the amount of p-methoxy phenol or Fe is small, and therefore there is almost no coloration problem.

[4] Use of Water Absorbent Resin

Applications of the water absorbent resin that is obtained by the production method of the invention are not particularly limited, and preferably, it may be used in absorbing articles such as a hygiene product including a disposable diaper, a sanitary napkin, and an incontinent pad, a water retaining material for agricultural and horticultural use, an agent for solidifying waste liquid, or a water stopping agent for industrial use.

The water absorbent resin obtained by the invention exhibits particularly excellent performance when it is used in an absorbing article using water absorbent resin at high concentration. Content of the water absorbent resin in the absorber in these absorbing articles (core concentration) is preferably from 30 to 100% by weight, more preferably from 40 to 100% by weight, still more preferably from 50 to 100% by weight, further still more preferably from 60 to 100% by weight, particularly preferably from 70 to 100% by weight, and most preferably from 75 to 95% by weight. By containing the core concentration in the above-described amount, effect of the invention is exerted still more significantly, which is preferable. For example, in the case where the water absorbent resin obtained by the invention is used in the range of the core concentration, in particular, at the upper layer of the absorbent core, the core exhibits superior capability of spreading of liquid such as urine due to the high liquid permeability (liquid permeability against pressure), and, absorbing amount of the absorbing articles, such as disposable diaper, in total is enhanced due to the efficient liquid distribution, therefore that is preferable. Further, it is also preferable that the invention provides absorbing articles which can maintain white color showing cleanliness.

In addition, it is preferable that the above absorbent material is compression molded so as to have a density of 0.06 to 0.50 [$g/cm^3$], and a basis weight of 0.01 to 0.20 [$g/cm^2$]. Thickness of the above absorbent material is preferably 30 mm or less, more preferably 20 mm or less, and still more preferably 10 mm or less, and thus the absorbent articles suitable for a thin-type disposable diaper can be provided.

EXAMPLES

Herein below, the invention is described in view of the Examples and the Comparative examples. However, the invention should not be construed to be limited by them. For the sake of convenience, "liter" may be described as "L" and "% by weight" may be described as "wt %". Meanwhile, various physical properties that are described in the examples are obtained by the following measurement method under the condition including room temperature (20 to 25° C.) and humidity of 50 RH %, unless specifically described otherwise.

[1] Amount of Peroxides Relative to Solid Content in Hydrogel

To a polypropylene container with a cap (volume; 260 mL), 3 g of hydrogel as a sample and 100 g of 5% by weight aqueous sodium chloride solution (if gel is swelled and is not stirred, salt concentration or amount of aqueous solution is suitably adjusted) were added and stirred at 500 rpm by using a Teflon (registered trademark) coated 25 mm stirrer at room temperature in the dark. Two hours later, the solution was taken out and passed through a filter (GL CHROMATO DISK, manufactured by GL Sciences Inc., water-type 25A, pore diameter of 0.45 µm). 5.00 g of the resultant solution was added to a glass sample bottle with a screw cap (volume of 50 mL; diameter of 35 mm; height of about 80 mm). After that, 0.50 g of 44% by weight potassium iodide solution was immediately added thereto and stirred in the dark at room temperature. One hour later, the solution was transferred to 1 cm plastic cell and the absorbance (detection wavelength: 350 nm) was measured by using a spectrophotometer (U-1100 Hitachi Ratio Beam Spectrophotometer) (absorbance of 5 g of 5% by weight of sodium chloride solution added with 0.50 g of 44% by weight potassium iodide solution was set to 0 (blank)). 5% by weight sodium chloride solutions each containing peroxide in an amount of 0 ppm (not-added), 5 ppm, 10 ppm, 15 ppm, or 20 ppm were prepared and absorbances were obtained as above to establish a calibration curve. From the absorbance of sample and the calibration curve obtained, amount of peroxide (ppm) in the sample hydrogel was calculated.

The peroxide in the water absorbent resin after drying can be measured in the same manner as above. Although the measurement limit is suitably determined based on the amount of polymer and sensitivity, or the like, in the case of the hydrogel and water absorbent resin of the invention, the limit is generally 0.5 ppm and an amount less than the detection limit (for example, 0.5 ppm) is designated as N.D (Non-Detectable).

[2] Solid Content Concentration (Resin Solid Content)

In an aluminum cup with bottom surface diameter of about 50 mm, 1.00 g of the water absorbent resin was weighed and total weight W1 [g] of a sample (including the water absorbent resin and aluminum cup) was precisely weighed.

Subsequently, the sample was placed in an oven at the atmospheric temperature of 180° C. to dry the water absorbent resin. Three hours later, the sample was taken out of the oven and then cooled to room temperature in a desiccator. After that, the total weight W2 [g] of a sample after drying (including the water absorbent resin and aluminum cup) was weighed and the solid content concentration (unit; [% by weight]) was calculated according to the following Formula.

[Expression 2]

Solid content concentration [% by weight]=100−{($W1-W2$)/(Weight of water absorbent resin [g])×100} [Formula 2]

Meanwhile, the measurement of solid content concentration in particulate hydrogel crosslinked polymer (i.e., resin solid content concentration) was carried out in the same manner as above except that the using amount of hydrogel is changed to about 2 to 4 g and the drying time was changed to 24 hours.

[3] SFC (Saline Flow Conductivity)

SFC (saline flow conductivity) of the water absorbent resin obtained according to the invention was measured by the method described in U.S. Pat. No. 5,669,894.

[4] GEX Value

A GEX value of the water absorbent resin obtained by the invention was calculated according to the description of US Patent Application Publication No. 2006/0167198. Letting y [g/g] be the value of CRC (water absorption capacity without load) and x [% by weight] be the amount of Ext (water extractables), the GEX value is defined by the following formulae below.

[Expression 3]

$GEX$ value $(x>1)=(y+17)/\ln(x)$ [Formula 3]

[Expression 4]

$GEX$ value $(x \leq 1)=y/x$ [Formula 4]

The GEX value is a parameter to evaluate the relation between two contradictory physical properties (CRC and Ext) of the water absorbent resin unambiguously, and the greater the GEX value, the better the performance of the water absorbent resin.

[5] Other Physical Properties

Physical properties such as a CRC (water absorption capacity without load), particle size distribution (see, the "PSD" section above: method disclosed in ERT 420.2-02), pH extractables (see the "Ext" section above; method disclosed in ERT 470.2-02), and amount of residual acrylic acid (see the "Residual monomers" section above; method disclosed in ERT 410.2-02) of the water absorbent resin were measured in accordance with EDANA ERT or US Patent Application Publication No. 2006/204755.

Production Example 1

With reference to the Examples 3 of U.S. Pat. No. 6,906,159, acrylic acid salt having monomer concentration of 55% by weight and neutralization rate of 60% by mole was polymerized by UV ray. By crushing the gel with a vertical type crusher, a hydrogel crosslinked polymer was obtained.

Specifically, a mixture solution (A) containing 139.5 g of acrylic acid, 0.09 g of polyethylene glycol diacrylate (number average molecular weight of 478), and 0.02 g of 2-hydroxy-2-methyl-1-phenyl-propan-1-one, and, NaOH aqueous solution (B) in which 95.8 g of 48.5% by weight NaOH aqueous solution was diluted with 61.2 g of ion exchange water and added with 0.02 g of diethylenetriamine pentaacetic acid • pentasodium salt, were prepared separately, and deaerated for 30 minutes under nitrogen gas atmosphere. The NaOH solution (B) was stirred using a magnetic stirrer and the solution (A) was added thereto all at once in an open system. After mixing, an aqueous solution of monomer was obtained. Although precipitates were observed at the initial stage of mixing, they were quickly dissolved, and the liquid temperature increased to about 90° C. by heat of neutralization and dissolution. The monomer concentration in the aqueous solution of monomer obtained was 55% by weight and the neutralization rate was 60% by mole.

Subsequently, 0.58 g of 10% by weight of sodium persulfate solution (0.03 g of sodium persulfate per 1 mole of the monomer) was added to the monomer solution. After stirring for several seconds the mixture was immediately poured into a stainless tray container (surface temperature; about 64° C.) which has been placed on a hot plate heated to 90° C. (thickness of the solution; about 5 mm) in an open system. The stainless tray container had a size as follows: bottom surface 200×260 mm, top surface 560×460 mm, height 140 mm, trapezoidal at the central cross-section, and open at the top. A silicone sheet was adhered on an inner wall of the stainless tray container. Immediately thereafter, ultraviolet light was irradiated with a black light mercury lamp (peak wavelength of 352 nm, model No. H400BL, fitted within a projector MT-4020, both the lamp and the projector were products of TOSHIBA LIGHTING & TECHNOLOGY CORPORATION) to initiate polymerization. While the polymerization proceeded with generating water vapor, expanding in all directions and foaming, and then the polymerization system shrank to almost the same size as the original. The hydrogel crosslinked polymer crept up the tilt of the sides of the container when expanding, and then, the hydrogel crosslinked polymer stopped its movements at the state that it was larger than the size of the bottom of the container, when shrinking, but, it returned toward their original places. The resultant polymer expanded to about 30 times as large as the volume of the aqueous monomer solution at the maximum. The expansion and shrinkage ended within about 1 minute and, when the UV irradiation for 2 minutes had been completed, the hydrogel crosslinked polymer was taken out. From the record of the change in temperature of the polymerization system, the polymerization initiation temperature was 88° C. and the highest temperature was 111° C. The resultant hydrogel crosslinked polymer was in a much wrinkly because the bubbles either as is or collapsed, according to the size of bubbles.

The hydrogel crosslinked polymer obtained by the polymerization step described above was crushed with VERTICAL PULVERIZER (model No. VM27-S produced by Orient Co., Ltd., screen opening size of 12 mm), thus obtaining particulate hydrogel crosslinked polymer (1) having fluidity. The obtained particulate hydrogel crosslinked polymer (1) had a CRC of 33 [g/g], a water extractables of 6% by weight, a residual monomer content of 600 ppm, solid content concentration of 70% by weight, and weight average particle diameter (D50) of 2.5 mm. Sodium persulfate in the particulate hydrogel crosslinked polymer (1) was 280 ppm relative to the solid content.

Comparative Example 1

Subsequently, 2 kg of the particulate hydrogel crosslinked polymer (1) (containing 280 ppm sodium persulfate relative to the solid content/index of the thermally degradable radical polymerization initiator content is 21.0) obtained by plural polymerizations (Production example 1) was placed on a punching plate (material was SUS 304; hole was oval and staggered, width of 1.2 mm, length of 15 mm; hole area ratio was 27%; size 15 cm×15 cm) and dried to obtain comparative dried product (1). The drying was carried out by blowing hot air of temperature of 170° C. and dew point of 5° C. from the bottom to the top of the punching plate for 20 minutes at blowing speed of 1.6 [m/sec].

After drying, the comparative dried product (1) was pulverized with a roll mill and the resulting pulverized product was subjected to size classification by using JIS standard sieve with sieve mesh size of 600 μm and 300 μm. As a result, comparative water absorbent resin (1) mostly having particle size of from 300 to 600 μm was obtained. Various physical properties including CRC of the comparative water absorbent resin (1) obtained are summarized in Table 1.

Comparative Example 2

Subsequently, 2 kg of the particulate hydrogel crosslinked polymer (1) obtained from the Production example 1 was placed on a punching plate and hot air with temperature of 140° C. and dew point of 75° C. was blown from the bottom to the top of the punching plate for 4 minutes at blowing speed of 1.6 [m/sec]. After blowing air, the sodium persulfate remaining in the particulate hydrogel crosslinked polymer was 180 ppm relative to the solid content. In the Comparative example 2, index of the thermally degradable radical polymerization initiator content was 13.5.

Thereafter, except that hot air with temperature of 170° C. and dew point of 5° C. was blown from the top to the bottom of the punching plate for 20 minutes at blowing speed of 1.6 [m/sec], the drying operation was carried out in the same manner as the Comparative example 1 to obtain comparative product (2).

After the drying, comparative dried product (2) was pulverized with a roll mill and the resulting pulverized product was subjected to size classification in the same manner as the Comparative example 1. As a result, comparative water absorbent resin (2) mostly having particle size of from 300 to 600 μm was obtained. Various physical properties of comparative water absorbent resin (2) obtained are summarized in Table 1.

Example 1

2 kg of the particulate hydrogel crosslinked polymer (1) obtained from the Production example 1 (containing 280 ppm sodium persulfate relative to the solid content) was placed on the punching plate and maintained for 30 minutes under no air stream condition, the temperature of 100° C. and the dew point of 85° C. [step for reducing peroxide]. 30 minutes later, the sodium persulfate remaining in the particulate hydrogel crosslinked polymer was 95 ppm relative to the solid content. In the Example 1, index of the thermally degradable radical polymerization initiator content was 7.12.

Thereafter, except that hot air with temperature of 170° C. and dew point of 5° C. was blown from the bottom to the top of the punching plate for 20 minutes at blowing speed of 1.6 [m/sec], the drying operation was carried out in the same manner as the Comparative example 1 to obtain dried product (1).

After drying, dried product (1) was pulverized with a roll mill and the resulting pulverized product was subjected to size classification in the same manner as the Comparative example 1. As a result, water absorbent resin (1) mostly having particle size of from 300 to 600 μm was obtained. Various physical properties of water absorbent resin (1) obtained are summarized in Table 1.

Comparative Example 3

2 kg of the particulate hydrogel crosslinked polymer (1) obtained from Production example 1 (containing 280 ppm sodium persulfate relative to the solid content) was placed on the punching plate and maintained for 30 minutes under no air stream condition, the temperature of 100° C. and the dew point of 85° C. 30 minutes later, the sodium persulfate remaining in the particulate hydrogel crosslinked polymer was 95 ppm relative to the solid content. In Comparative example 3, index of the thermally degradable radical polymerization initiator content was 7.12.

Thereafter, except that hot air with temperature of 140° C. and dew point of 5° C. was blown from the bottom to the top of the punching plate for 20 minutes at blowing speed of 1.6 [m/sec], the drying operation was carried out in the same manner as the Comparative example 1 to obtain comparative dried product (3).

After drying, it was tried to pulverized comparative dried product (3) with a roll mill in the same manner as the Comparative example 1. However, there were non-dried products which strongly adhered onto the surface of the roll mill, and therefore it was impossible to crush them.

Comparative Example 4

2 kg of the particulate hydrogel crosslinked polymer (1) obtained from the Production example 1 (containing 280 ppm sodium persulfate relative to the solid content) was placed on the punching plate and maintained for 30 minutes under no air stream condition, the temperature of 100° C. and the dew point of 85° C. 30 minutes later, the sodium persulfate remaining in the particulate hydrogel crosslinked polymer was 95 ppm relative to the solid content. In the Comparative example 4, index of the thermally degradable radical polymerization initiator content was 7.12.

Thereafter, except that hot air with temperature of 140° C. and dew point of 5° C. was blown from the bottom to the top of the punching plate for 60 minutes at blowing speed of 1.6 [m/sec], the drying operation was carried out in the same manner as the Comparative example 1 to obtain comparative dried product (4).

After the drying, comparative dried product (4) was pulverized with a roll mill and the resulting pulverized product was subjected to size classification in the same manner as the Comparative example 1. As a result, comparative water absorbent resin (4) mostly having particle size of from 300 to 600 μm was obtained. No products were found to be adhered because of non-dried products, on the surface of the roll mill during crushing. Various physical properties of comparative water absorbent resin (4) obtained are summarized in the Table 1. CRC was found to have a low value.

Example 2

2 kg of the particulate hydrogel crosslinked polymer (1) obtained from the Production example 1 (containing 280 ppm sodium persulfate relative to the solid content) was placed on the punching plate and hot air with temperature of 140° C. and dew point of 75° C. was blown from the bottom to the top of the punching plate for 10 minutes at blowing speed of 1.6 [m/sec]. After blowing air, the sodium persulfate remaining in the particulate hydrogel crosslinked polymer was 40 ppm relative to the solid content. In Example 2, index of the thermally degradable radical polymerization initiator content was 3.00.

Thereafter, except that hot air with temperature of 170° C. and dew point of 5° C. was blown from the top to the bottom of the punching plate for 20 minutes at blowing speed of 1.6 [m/sec], the drying operation was carried out in the same manner as the Comparative example 1 to obtain dried product (2).

After drying, dried product (2) was pulverized with a roll mill and the resulting pulverized product was subjected to size classification in the same manner as the Comparative example 1. As a result, water absorbent resin (2) mostly having particle size of from 300 to 600 μm was obtained. Various physical properties of water absorbent resin (2) obtained are summarized in Table 1.

Example 3

2 kg of the particulate hydrogel crosslinked polymer (1) obtained from Production example 1 (containing 280 ppm sodium persulfate relative to the solid content) was placed on the punching plate and hot air with temperature of 140° C. and dew point of 75° C. was blown from the bottom to the top of the punching plate for 7 minutes at blowing speed of 1.6 [m/sec]. After blowing air, the sodium persulfate remaining in the particulate hydrogel crosslinked polymer was 80 ppm relative to the solid content. In the Example 3, index of the thermally degradable radical polymerization initiator content was 6.00.

Thereafter, except that hot air with temperature of 170° C. and dew point of 5° C. was blown from the top to the bottom of the punching plate for 20 minutes at blowing speed of 1.6 [m/sec], the drying operation was carried out in the same manner as the Comparative example 1 to obtain dried product (3).

After drying, dried product (3) was pulverized with a roll mill and the resulting pulverized product was subjected to size classification in the same manner as the Comparative example 1. As a result, water absorbent resin (3) mostly having particle size of from 300 to 600 μm was obtained. Various physical properties of water absorbent resin (3) obtained are summarized in Table 1.

Example 4

2 kg of the particulate hydrogel crosslinked polymer (1) obtained from Production example 1 (containing 280 ppm sodium persulfate relative to the solid content) was placed on the punching plate and hot air with temperature of 120° C. and dew point of 75° C. was blown from the bottom to the top of the punching plate for 10 minutes at blowing speed of 1.6 [m/sec]. After blowing air, the sodium persulfate remaining in the particulate hydrogel crosslinked polymer was 100 ppm. In Example 4, index of the thermally degradable radical polymerization initiator content was 7.50.

Thereafter, except that hot air with temperature of 170° C. and dew point of 5° C. was blown from the top to the bottom of the punching plate for 20 minutes at blowing speed of 1.6 [m/sec], the drying operation was carried out in the same manner as the Comparative example 1 to obtain dried product (4).

After the drying, dried product (4) was pulverized with a roll mill and the resulting pulverized product was subjected to size classification in the same manner as the Comparative example 1. As a result, water absorbent resin (4) mostly having particle size of from 300 to 600 μm was obtained. Various physical properties of water absorbent resin (3) obtained are summarized in Table 1.

TABLE 1

|  |  | Comparative example 1 Comparative water absorbent resin (1) | Comparative example 2 Comparative water absorbent resin (2) | Example 1 Water absorbent resin (1) | Comparative example 3 Comparative water absorbent resin (3) | Comparative example 4 Comparative water absorbent resin (4) | Example 2 Water absorbent resin (2) | Example 3 Water absorbent resin (3) | Example 4 Water absorbent resin (4) |
| --- | --- | --- | --- | --- | --- | --- | --- | --- | --- |
| CRC | [g/g] | 48 | 45 | 43 | — | 34 | 44 | 43 | 43 |
| Water Extractables | [wt %] | 24 | 19 | 14 | — | 9 | 14 | 14 | 14 |
| Residual monomers | [ppm] | 200 | 200 | 150 | — | 200 | 150 | 160 | 160 |
| GEX value | [—] | 20.5 | 21.1 | 22.7 | — | 23.2 | 23.1 | 22.7 | 22.7 |

Production Example 2

Using line mixing, a solution of acrylic acid partial sodium salt (monomer concentration of 53% by weight) of neutralization rate of 70% by mole containing 0.03% by mole of polyethylene glycol diacrylate (relative to the monomer) as an internal crosslinking agent was continuously mixed with 0.04 g of sodium persulfate (relative to 1 mol of the monomer) and 100 ppm of diethylenetriamine pentaacetic acid • pentasodium salt. After that, the mixture was fed to a belt polymerization reactor to perform aqueous solution polymerization.

The hydrogel crosslinked polymer obtained by the aqueous solution polymerization step described above was crushed with VERTICAL PULVERIZER (model No. VM27-S produced by Orient Co., Ltd., screen 12 mm), thus obtaining particulate hydrogel crosslinked polymer (2) having fluidity. The particulate hydrogel crosslinked polymer (2) had CRC of 20 [g/g], a water extractable content of 2.4% by weight, a residual monomer content of 5000 ppm, solid content concentration of 69% by weight, and weight average particle diameter (D50) of 2.4 mm. Sodium persulfate in particulate hydrogel crosslinked polymer (2) was 370 ppm relative to the solid content.

Comparative Example 5

The particulate hydrogel crosslinked polymer (2) obtained from the Production example 2 (containing 370 ppm sodium persulfate relative to the solid content/index of the thermally degradable radical polymerization initiator content is 28.5)

was introduced to a continuous through-circulation belt dryer with a traverse feeder and dried to obtain comparative dried product (5).

The drying was carried out such that, by sequential control of the traverse feeder, the particulate hydrogel crosslinked polymer (2) was continuously laminated on the constantly-operating through-circulation belt (punching metal). The drying time was 35 min. The dryer and other drying conditions are as described in the following (a) to (c).

(a) Continuous Through-Circulation Belt Dryer

As continuous through-circulation belt dryer, a dryer having total six chambers which have the same volume and individually controllable temperature setting was used. The transit time for each drying chamber was about 5.8 minutes (35 minutes on through-circulation belt/6 chambers).

(b) Temperature and Air Speed of Hot Air

Hot air introduced to each drying chamber was set to have temperature of 180° C., dew point of 10° C., and air speed of 1.6 [m/sec]. Direction of the hot air was from the bottom to the top of the dryer for the first chamber, while it was from the top to the bottom of the dryer for the second chamber to the sixth chamber.

(c) Through-Circulation Belt

As through-circulation belt, SUS 304 stainless belt was used, and the belt was a punching metal having oval and staggered holes with width of 1.2 mm and length of 15 mm and hole area ratio of 27%.

After drying, the entire amount of comparative dried product (5) was continuously supplied to a three-level roll mil (roll gap; from the top, 1.0 mm/0.55 mm/0.42 mm) for pulverizing. Thereafter, the size classification was carried out by using a screening device having wire mesh with a sieve mesh size of 850 μm. As a result, comparative water absorbent resin (5) was obtained. Various physical properties including CRC and the like of comparative water absorbent resin (5) obtained are summarized in Table 2.

Subsequently, a surface crosslinking agent solution consisting of 0.6 parts by weight of propylene glycol, 0.3 parts by weight of 1,4-butanediol, and 3 parts of water relative to 100 parts by weight of comparative water absorbent resin (5), was sprayed to comparative water absorbent resin (5) and mixed until it was homogeneous. The mixture was then subjected to heat treatment at 200° C. for 40 minutes to obtain comparative water absorbent resin (5) with surface crosslinked.

35 g of the comparative water absorbent resin (5) with crosslinked surface and 10 g of glass beads having diameter of 6 mm were added into a 225 mL mayonnaise bottle, and as a process model for impact resistance, it was shaken for 10 minutes by using a paint shaker (manufactured by TOYO SEIKI SEISAKU-SHA LTD.). Subsequently, 0.3 g of a liquid permeability improving agent, which included 1.0 parts by weight of 50% by weight aluminum sulfate solution, 0.025 parts by weight of propylene glycol and 0.3 parts by weight of sodium lactate, relative to 100 parts by weight of the comparative water absorbent resin particles (5), was added to 30 g of the comparative water absorbent resin particles (5) obtained after shaking, and mixed. Then, the mixture was cured for 30 minutes at 60° C. After curing, it was added to 225 ml mayonnaise bottle containing 10 g of glass beads having diameter of 6 mm and shaken for 10 minutes by using the paint shaker to obtain comparative aluminum surface treated product (5). Physical properties of the comparative aluminum surface treated product (5) obtained are given in Table 2. The amount of persulfate in the comparative aluminum surface treated product (5) was N.D. and the residual monomer was 380 ppm.

Example 5

Except that using amount of polyethylene glycol diacrylate as an internal crosslinking agent is changed to 0.02% by mole (relative to the monomer), the aqueous solution polymerization and gel crushing were carried out in the same manner as the Production example 2 to obtain particulate hydrogel crosslinked polymer (3) having fluidity. The particulate hydrogel crosslinked polymer (3) had CRC of 23 [g/g], a water extractable content of 2.6% by weight, a residual monomer content of 4500 ppm, solid content concentration of 69% by weight, and weight average particle diameter (D50) of 2.4 mm. Sodium persulfate in particulate hydrogel crosslinked polymer (3) was 370 ppm relative to the solid content.

Particulate hydrogel crosslinked polymer (3) obtained from above (containing 370 ppm sodium persulfate relative to the solid content) was introduced to a continuous through-circulation belt dryer in the same manner as the Comparative example 5. For the first chamber of the continuous through-circulation belt dryer, hot air with temperature of 140° C. and dew point of 75° C., in which the dew point was controlled by adding water vapor, was blown from the bottom to the top of the dryer at air speed of 1.6 [m/sec]. For the second and subsequent chambers, drying was carried out under the same drying condition as the Comparative example 5 (temperature of 180° C.; air speed of 1.6 [m/sec]; direction of hot air was, for the first chamber, from the bottom to the top of the dryer, and for the second to the sixth chambers, from the top to the bottom of the dryer) to obtain dried product (5).

Between the first chamber and the second chamber of the continuous through-circulation belt dryer, the hydrogel crosslinked polymer was sampled from the top of the dryer. As a result of the measurement, it was found that sodium persulfate remaining in the particulate hydrogel crosslinked polymer was 95 ppm relative to the solid content. In the Example 5, index of the thermally degradable radical polymerization initiator content was 7.33.

The entire amount of dried product (5) was crushed and subjected to the size classification in the same manner as the Comparative example 5 to obtain water absorbent resin (5). No products were found to be adhered because of non-dried products on the surface of a roll mill after crushing. Various physical properties of water absorbent resin (5) obtained are summarized in Table 2.

Water absorbent resin (5) was subjected to the surface crosslinking and the aluminum surface treatment in the same manner as the Comparative example 5 to obtain aluminum surface treated product (5). Various physical properties of aluminum surface treated product (5) obtained are summarized in Table 2. The amount of persulfate in aluminum surface treated product (5) was N.D. and the residual monomer was 190 ppm.

Example 6

Particulate hydrogel crosslinked polymer (3) obtained from Example 5 (containing 370 ppm sodium persulfate relative to the solid content) was introduced to a continuous through-circulation belt dryer in the same manner as the Comparative example 5. For the first to the sixth chambers (entire chambers) of the continuous through-circulation belt dryer, hot air with temperature of 100° C. and dew point of 5° C. was blown from the bottom to the top of the dryer at air speed of 1.6 [m/sec]. It was further introduced to the continuous through-circulation belt dryer which was set to have same condition as Comparative example 5 (temperature of 180° C.; air speed of 1.6 [m/sec]; direction of hot air was, for the first chamber, from the bottom to the top of the dryer, and for the second to the sixth chambers, from the top to the bottom of the dryer) to obtain dried product (6). The amount of sodium persulfate in the particulate hydrogel crosslinked polymer after being blown with hot air with 100° C. was 80 ppm relative to the solid content, and in Example 6, index of the thermally degradable radical polymerization initiator content was 6.17.

The entire amount of dried product (6) was crushed and subjected to the size classification in the same manner as the Comparative example 5 to obtain water absorbent resin (6). No products were found to be adhered because of non-dried products on the surface of a roll mill after crushing. Various physical properties of water absorbent resin (6) obtained are summarized in Table 2.

Water absorbent resin (6) was subjected to the surface crosslinking and the aluminum surface treatment in the same manner as the Comparative example 5 to obtain aluminum surface treated product (6). Various physical properties of aluminum surface treated product (6) obtained are summarized in Table 2.

TABLE 2

|  |  | Comparative example 5 | Example 5 | Example 6 |
|---|---|---|---|---|
|  |  | Comparative water absorbent resin (5) | Water absorbent resin (5) | Water absorbent resin (6) |
| CRC | [g/g] | 39 | 38 | 39 |
| Water Extractables | [wt %] | 15 | 11 | 12 |
| Residual monomers | [ppm] | 400 | 200 | 450 |
| GEX value | [—] | 20.7 | 22.9 | 22.5 |
|  |  | Comparative aluminum surface treated product (5) | Aluminum surface treated product (5) | Aluminum surface treated product (6) |
| Residual monomers | [ppm] | 380 | 190 | — |
| Amount of peroxides | [ppm] | N.D | N.D | — |
| CRC | [g/g] | 28 | 28 | 28 |
| SFC | *1 | 94 | 128 | 122 |

*1: [× $10^{-7}$ · $cm^3$ · s · $g^{-1}$]

Production Example 3

In a kneader having two sigma shape blades, an acrylate monomer solution consisting of sodium acrylate, acrylic acid, and water (monomer concentration was 38% by weight and neutralization rate was 75% by mole) was prepared and, as an internal crosslinking agent, polyethylene glycol diacrylate was dissolved therein to have the concentration of 0.06% by mole relative to the monomer.

Thereafter, the aqueous solution was purged with nitrogen gas so that the oxygen concentration in aqueous solution was lowered and also the whole reaction vessel was replaced with nitrogen. Subsequently, while rotating the two sigma shape blades, as a polymerization initiator, 0.12% by mole (relative to the monomer) of sodium persulfate and 0.0006% by mole (relative to the monomer) of L-ascorbic acid were added and the stir polymerization was performed in the kneader. 40 minutes later, The particulate hydrogel crosslinked polymer (4) was obtained. Particulate hydrogel crosslinked polymer (4) had CRC of 25 [g/g], a water extractable content of 2.5% by weight, a residual monomer content of 5500 ppm, solid content concentration of 40% by weight, and weight average particle diameter (D50) of 2 mm. Sodium persulfate in particulate hydrogel crosslinked polymer (4) was 1320 ppm relative to the solid content.

Comparative Example 6

Subsequently, 2 kg of the particulate hydrogel crosslinked polymer (4) (containing 1320 ppm sodium persulfate per the solid content/index of the thermally degradable radical polymerization initiator content was 303) obtained by plural polymerizations (Production example 3), was placed on a punching plate (material was SUS 304; hole was oval and staggered, width of 1.2 mm, length of 15 mm; hole area ratio was 27%; size was 15 cm×15 cm) and dried to obtain comparative dried product (6). The drying was carried out by blowing hot air with temperature of 180° C. and dew point of 5° C. from the bottom to the top of the punching plate for 30 minutes at blowing speed of 1.6 [m/sec].

After drying, comparative dried product (6) was pulverized with a roll mill and the resulting pulverized product was subjected to size classification by using JIS standard sieve with mesh size of 600 µm or 300 µm. As a result, comparative water absorbent resin (6) mostly having particle size of from 300 to 600 µm was obtained. Various physical properties including CRC of the comparative water absorbent resin (6) obtained are summarized in Table 3.

Subsequently, a surface crosslinking agent solution consisting of 0.6 parts by weight of propylene glycol, 0.3 parts by weight of 1,4-butanediol, and 3 parts of water relative to 100 parts by weight of comparative water absorbent resin (6), was sprayed to comparative water absorbent resin (6) and mixed until it was homogeneous. The mixture was then subjected to heat treatment at 200° C. for 40 minutes to obtain comparative water absorbent resin (6) surface crosslinked.

35 g of comparative water absorbent resin (6) with surface crosslinked and 10 g of glass beads having diameter of 6 mm were added into a 225 mL mayonnaise bottle, and as a process model for impact resistance, it was shaken for 10 minutes by using a paint shaker (manufactured by TOYO SEIKI SEISAKU-SHA LTD.). Subsequently, 0.3 g of a liquid permeability improving agent, in which the liquid permeability improving agent consisted of 1.0 parts by weight of 50% by weight aluminum sulfate solution, 0.025 parts by weight of propylene glycol and 0.3 parts by weight of sodium lactate, relative to 100 parts by weight of the comparative water absorbent resin particles (6), was added to 30 g of the comparative water absorbent resin particles (6) obtained after shaking and mixed. Then, the mixture was cured for 30 minutes at 60° C. After curing, it was added to 225 ml mayonnaise bottle containing 10 g of glass beads having diameter of 6 mm and shaken for 10 minutes by using the paint shaker to obtain comparative aluminum surface treated product (6). Physical properties of the comparative aluminum surface treated product (6) obtained are given in Table 3.

Comparative Example 7

Except that using amount of polyethylene glycol diacrylate as an internal crosslinking agent is changed to 0.05% by mole (relative to the monomer), the aqueous solution polymerization was carried out in the same manner as the Production example 3 to obtain particulate hydrogel crosslinked polymer (5). The particulate hydrogel crosslinked polymer (5)

obtained had CRC of 26 [g/g], a water extractable content of 2.6% by weight, a residual monomer content of 5800 ppm, solid content concentration of 40% by weight, and weight average particle diameter (D50) of 1.9 mm. Sodium persulfate in particulate hydrogel crosslinked polymer (5) was 370 ppm relative to the solid content.

Subsequently, 2 kg of the particulate hydrogel crosslinked polymer (5) obtained from above (containing 370 ppm sodium persulfate relative to the solid content) was placed on the punching plate and hot air with temperature of 140° C. and dew point of 75° C. was blown from the bottom to the top of the punching plate for 20 minutes at blowing speed of 1.6 [m/sec]. After blowing air, the sodium persulfate remaining in the particulate hydrogel crosslinked polymer was 90 ppm relative to the solid content. In the Comparative example 7, index of the thermally degradable radical polymerization initiator content was 20.7.

Thereafter, except that hot air with temperature of 180° C. and dew point of 5° C. was blown from the top to the bottom of the punching plate for 30 minutes at blowing speed of 1.6 [m/sec], the drying operation was carried out in the same manner as the Comparative example 6 to obtain comparative dried product (7).

After drying, comparative dried product (7) was pulverized with a roll mill and the resulting pulverized product was subjected to size classification in the same manner as the Comparative example 6. As a result, comparative water absorbent resin (7) mostly having particle size of from 300 to 600 µm was obtained. Various physical properties of comparative water absorbent resin (7) obtained are summarized in Table 3.

Comparative water absorbent resin (7) was subjected to the surface crosslinking and the aluminum surface treatment in the same manner as the Comparative example 6 to obtain comparative aluminum surface treated product (7). Various physical properties of comparative aluminum surface treated product (7) obtained are summarized in Table 3. The amount of persulfate in comparative aluminum surface treated product (7) was N.D. and the residual monomer was 235 ppm.

Comparative Example 8

To a polypropylene container covered with foamed styrol as a heat insulating material (inner diameter of 80 mm, volume of 1 liter), to mixture solution (A) containing 276.9 g of acrylic acid, 0.90 g (0.045% by mole, relative to the monomer) of polyethylene glycol diacrylate, and 1.68 g of 1.0% by weight diethylenetriamine pentaacetic acid • pentasodium salt, solution (B) in which 221.81 g of 48.5% by weight NaOH solution is diluted with 183.4 g of ion exchange water adjusted to the temperature of 50° C., was rapidly added and mixed in an open system under stirring by a magnetic stirrer. As a result, an aqueous solution of monomer having the liquid temperature increased to about 102° C. due to heat generated by neutralization and dissolution was obtained.

Subsequently, after waiting till the monomer solution obtained reached 96° C., 15.4 g of 3% by weight of sodium persulfate solution was added thereto. After stirring for several seconds, it was heated until the surface temperature was 100° C. by using a hot plate (NEO HOT PLATE H1-1000, manufactured by IuchiSeieido Co.). Then, in an open system, the mixture was poured into a stainless tray container having bottom surface 250×250 mm, in which the inside of the container was coated with Teflon (registered trademark). The stainless tray container has a size as follows: bottom surface 250×250 mm, top surface 640×640 mm, height 50 mm, trapezoidal at the central cross-section, and open at the top.

Soon after poured into the tray, the aqueous monomer solution underwent polymerization. The polymerization proceeded while generating water vapor and expanding in all directions and foaming. And then, the polymerization system shrank to the size that was slightly larger than the size of the bottom of the container. The expansion and the shrinkage were completed within 1 min. After maintaining the content in the polymerization container for 4 minutes, the hydrous polymer was discharged therefrom.

The hydrous polymer obtained was crushed by using a meat chopper with dice diameter of 9.5 mm (ROYAL MEAT CHOPPER VR400K, manufactured by IIZUKA Industrial Co.) to obtain micronized particulate hydrogel crosslinked polymer (6). The particulate hydrogel crosslinked polymer (6) obtained had CRC of 22 [g/g], a water extractable content of 2.3% by weight, a residual monomer content of 6500 ppm, solid content concentration of 53% by weight, and weight average particle diameter (D50) of 1.8 mm. Sodium persulfate in particulate hydrogel crosslinked polymer (6) was 1250 ppm relative to the solid content. The addition amount of the gel was about 340 [g/min], and crushing was performed by adding de-ionized water at the rate of 48 [g/min] together with addition of the gel.

Subsequently, 2 kg of the particulate hydrogel crosslinked polymer (6) (containing 1250 ppm sodium persulfate relative to the solid content/index of the thermally degradable radical polymerization initiator content was 163) obtained by plural polymerizations was placed on a punching plate (material was SUS 304; hole was oval and staggered, width of 1.2 mm, length of 15 mm; hole area ratio was 27%; size was 15 cm×15 cm) and the drying was carried out by blowing hot air with temperature of 180° C. and dew point of 5° C. from the bottom to the top of the punching plate for 30 minutes at blowing speed of 1.6 [m/sec]. As a result of drying, comparative dried product (8) was obtained.

After drying, comparative dried product (8) was pulverized with a roll mill and the resulting pulverized product was subjected to the size classification in the same manner as the Comparative example 6. As a result, comparative water absorbent resin (8) mostly having particle size of from 300 to 600 µm was obtained. Various physical properties of comparative water absorbent resin (8) obtained are summarized in Table 3.

Comparative water absorbent resin (8) was subjected to the surface crosslinking and the aluminum surface treatment in the same manner as the Comparative example 6 to obtain comparative aluminum surface treated product (8). Various physical properties of comparative aluminum surface treated product (8) obtained are summarized in Table 3.

Example 7

Except that using amount of polyethylene glycol diacrylate as an internal crosslinking agent was changed to 0.70 g (0.035% by mole relative to the monomer), the aqueous solution polymerization and gel crushing were carried out in the same manner as the Comparative example 8 to obtain particulate hydrogel crosslinked polymer (7). The particulate hydrogel crosslinked polymer (7) obtained had CRC of 24 [g/g], a water extractable content of 2.5% by weight, a residual monomer content of 6100 ppm, solid content concentration of 53% by weight, and weight average particle diameter (D50) of 1.8 mm. Sodium persulfate in particulate hydrogel crosslinked polymer (7) was 1190 ppm relative to the solid content.

Subsequently, 2 kg of the particulate hydrogel crosslinked polymer (7) obtained from above (containing 1190 ppm sodium persulfate relative to the solid content) was placed on the punching plate and hot air with temperature of 140° C. and dew point of 75° C. was blown from the bottom to the top of the punching plate for 20 minutes at blowing speed of 1.6 [m/sec]. After blowing air, the sodium persulfate remaining in the particulate hydrogel crosslinked polymer was 95 ppm relative to the solid content. In Example 7, index of the thermally degradable radical polymerization initiator content was 12.4.

Thereafter, except that hot air with temperature of 180° C. and dew point of 5° C. was blown from the top to the bottom of the punching plate for 30 minutes at blowing speed of 1.6 [m/sec], the drying operation was carried out in the same manner as the Comparative example 8 to obtain dried product (7).

After drying, dried product (7) was pulverized with a roll mill and the resulting pulverized product was subjected to size classification in the same manner as the Comparative example 8. As a result, water absorbent resin (7) mostly having particle size of from 300 to 600 μm was obtained. Various physical properties of water absorbent resin (7) obtained are summarized in Table 3.

Water absorbent resin (7) was subjected to the surface crosslinking and the aluminum surface treatment in the same manner as the Comparative example 8 to obtain aluminum surface treated product (7). Various physical properties of aluminum surface treated product (7) obtained are summarized in Table 3. The amount of persulfate in aluminum surface treated product (7) was N.D. and the residual monomer was 160 ppm. Although not included in Table 3, the 150 μm pass through product was about 1% by weight, and the weight average particle diameter (D50) was about 400 μm.

problem like coloration. In this regard, compared to Patent Literature 28 or the like, the amount of peroxide in the hydrogel defined by the invention is lowered to 100 ppm (100 ppm relative to the solid content) or less when a hydrogel having solid content concentration of 45% by weight or more, preferably 50% by weight or more, more preferably 55% by weight or more, and still more preferably 60% by weight or more is dried, and as a result, GEX (a relationship between water absorption capacity and water extractables) or the like is further improved in the present invention.

Compared to conventional techniques, it is important in the invention that the persulfate salts are reduced when hydrogel having solid content concentration of 45% by weight or more, in particular 55% by weight or more, is dried. Thus, even when the hydrogel having high concentration (for example, 70% by weight) not disclosed in the examples of Patent Literature 28 is dried, excellent physical properties (GEX value) can be maintained.

In the Examples 1 to 4, the solid content concentration in the hydrogel after polymerization was 70% by weight, and water content was 42.9 g relative to 100 g of the water absorbent resin. Meanwhile, in Comparative examples 6 and 7, the solid content concentration was 40% by weight, and the water content was 150 g relative to 100 g of the water absorbent resin. Based on the results, it was found that the energy required for removing water is about 1/3.5 relative to Comparative examples and it is advantageous for $CO_2$ reduction, productivity, and cost performance. Especially when high

TABLE 3

|  |  | Comparative example 6 | Comparative example 7 | Comparative example 8 | Example 7 |
|---|---|---|---|---|---|
|  |  | Comparative water absorbent resin (6) | Comparative water absorbent resin (7) | Comparative water absorbent resin (8) | Water absorbent resin (7) |
| CRC | [g/g] | 36 | 37 | 37 | 36 |
| Water Extractables | [wt %] | 8 | 8 | 11 | 9 |
| Residual monomers | [ppm] | 330 | 250 | 320 | 180 |
| GEX value | [—] | 25.5 | 26.0 | 22.5 | 24.1 |
|  |  | Comparative aluminum surface treated product (6) | Comparative aluminum surface treated product (7) | Comparative aluminum surface treated product (8) | Aluminum surface treated product (7) |
| Residual monomers | [ppm] | — | 235 | — | 160 |
| Amount of peroxides | [ppm] | — | N.D | — | N.D |
| CRC | [g/g] | 29 | 29 | 28 | 28 |
| SFC | *2 | 78 | 80 | 81 | 101 |

*2: $[\times 10^{-7} \cdot cm^3 \cdot s \cdot g^{-1}]$

CONCLUSION

According to the technique disclosed in Patent Literature 28, index of thermally degradable radical polymerization initiator content is 40 to 100 for hydrogel by increasing the amount of thermally degradable radical polymerization initiator like persulfate salt during drying (Examples 1 to 7 of patent Literature 28 (persulfate salt relative to solid content: about 1233 to 2005 ppm in calculated value)) compared to conventional techniques or Comparative examples 1 to 5 of Patent Literature 28 (persulfate salt relative to solid content: about 782 to 983 ppm in calculated value). However, it has a concentration hydrogel including solid content concentration of 45% by weight or more is dried, superiority of the invention, which can maintain the physical properties, is clear.

According to Example 5 and Example 7, by using polyacrylic acid-type water absorbent resin having crosslinked surface, in particular the surface is crosslinked with a covalent surface crosslinking agent and an ionic bonding surface crosslinking agent (aluminum cation), a novel water absorbent resin which has water absorption capacity (CRC) of 5 [g/g] or more, residual monomer of 200 ppm or less, liquid permeability (SFC) of 100 $[\times 10^{-7} \cdot m \cdot s \cdot g^{-1}]$ or more, and peroxide amount of 1 ppm or less is provided.

INDUSTRIAL APPLICABILITY

According to the invention, for high concentration polymerization of water absorbent resin, a method for efficient drying of a water absorbent resin which has maintained/improved physical properties like CRC (centrifuge retention capacity) and Ext (water extractables) and has no non-dried product is provided. Thus, according to the invention, productivity for producing a water absorbent resin can be improved, production cost can be lowered, and energy required for production step can be reduced ($CO_2$ emission amount reduction), or the like.

It should be also noted that, the present application is based on Japanese Patent Application No. 2010-009812, filed on Jan. 20, 2010 and Japanese Patent Application No. 2010-084024 filed on Mar. 31, 2010, and the content of which is hereby incorporated by reference in its entirety into this application.

The invention claimed is:

1. A method for producing a water absorbent resin, comprising:
   a polymerization step to polymerize an unsaturated monomer, and;
   a drying step to dry a particulate hydrogel crosslinked polymer, which is obtained by micronization of a hydrogel polymer during or after the polymerization and which has a solid content concentration of 45% by weight or more,
   wherein,
   a through-circulation belt type dryer is used to perform the drying step,
   an amount of a peroxide in the particulate hydrogel crosslinked polymer to be dried in the drying step is 1 to 100 ppm relative to the weight of the solid content of the particulate hydrogel crosslinked polymer, and
   a drying temperature of the particulate hydrogel crosslinked polymer in the drying step is 170 to 190° C.

2. The production method according to claim 1, further comprising:
   a surface crosslinking step for surface crosslinking of a dried product obtained by the drying step.

3. The production method according to claim 2, wherein a saline flow conductivity (SFC) of the water absorbent resin is $10[\times 10^{-7} \cdot cm^3 \cdot s \cdot g^{-1}]$ or more after the surface crosslinking step.

4. The production method according to claim 2, wherein the heat treatment is carried out at 150 to 250° C. for the surface crosslinking step.

5. The production method according to claim 2, wherein a covalent surface crosslinking agent and an ionic bonding surface crosslinking agent are used in combination for the surface crosslinking step.

6. The production method according to claim 2, wherein a weight average particle diameter (D50) of the water absorbent resin before the surface crosslinking is from 200 to 600 μm and a ratio of the water absorbent resin having particle size of less than 150 μm before the surface crosslinking is 0 to 5% by weight.

7. The production method according to claim 1, further comprising:
   a step of reducing peroxide to perform a heat treatment of the particulate hydrogel crosslinked polymer at the temperature of less than 160° C. before the drying step, to reduce the amount of the peroxide in the particulate hydrogel crosslinked polymer.

8. The production method according to claim 7, further comprising:
   a surface crosslinking step for surface crosslinking of a dried product obtained by the drying step.

9. The production method according to claim 7, wherein a saline flow conductivity (SFC) of the water absorbent resin is $10 [\times 10^{-7} \cdot cm^3 \cdot s \cdot g^{-1}]$ or more after the surface crosslinking step.

10. The production method according to claim 7, wherein the heat treatment during the step of reducing peroxide is carried out in an atmosphere in which the dew point is from 50 to 100° C.

11. The production method according to claim 10, further comprising:
   a surface crosslinking step for surface crosslinking of a dried product obtained by the drying step.

12. The production method according to claim 10, wherein a saline flow conductivity (SFC) of the water absorbent resin is $10 [\times 10^{-7} \cdot cm^3 \cdot s \cdot g^{-1}]$ or more after the surface crosslinking step.

13. The production method according to claim 1, wherein the peroxide as a polymerization initiator for the polymerization step is used in an amount of 200 to 10000 ppm relative to total amount of the unsaturated monomer.

14. The production method according to claim 1, wherein the peroxide is a persulfate salt.

15. The production method according to claim 1, wherein the unsaturated monomer comprises acrylic acid as a main component, and the water absorbent resin is a polyacrylic acid (salt)-type water absorbent resin.

16. The production method according to claim 1, wherein a GEX value of the water absorbent resin before the surface crosslinking is 21 or more.

* * * * *